(12) United States Patent
Hedstrom et al.

(10) Patent No.: US 10,017,463 B2
(45) Date of Patent: *Jul. 10, 2018

(54) INHIBITORS OF DEUBIQUITINATING PROTEASES

(71) Applicant: Brandeis University, Waltham, MA (US)

(72) Inventors: Lizbeth K. Hedstrom, Auburndale, MA (US); Marcus J. Long, Lockington (GB); Ann Parrinello Lawson, Sudbury, MA (US)

(73) Assignee: Brandeis University, Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/327,861

(22) PCT Filed: Jul. 21, 2015

(86) PCT No.: PCT/US2015/041319
§ 371 (c)(1),
(2) Date: Jan. 20, 2017

(87) PCT Pub. No.: WO2016/014522
PCT Pub. Date: Jan. 28, 2016

(65) Prior Publication Data
US 2017/0204055 A1 Jul. 20, 2017

Related U.S. Application Data

(60) Provisional application No. 62/067,272, filed on Oct. 22, 2014, provisional application No. 62/027,066, filed on Jul. 21, 2014.

(51) Int. Cl.
*C07C 331/28* (2006.01)
*C07C 333/10* (2006.01)

(52) U.S. Cl.
CPC .......... *C07C 331/28* (2013.01); *C07C 333/10* (2013.01)

(58) Field of Classification Search
CPC ........................... C07C 331/28; C07C 333/10
See application file for complete search history.

(56) References Cited

U.S. PATENT DOCUMENTS

| | | | |
|---|---|---|---|
| 3,268,574 A | 8/1966 | Brotherton et al. | |
| 3,322,812 A | 5/1967 | Brotherton et al. | |
| 4,096,168 A | 6/1978 | Hallgren | |
| 5,539,123 A | 7/1996 | Digenis et al. | |
| 7,183,302 B2 * | 2/2007 | Romine | A61K 31/00 514/236.8 |
| 2009/0054430 A1 | 2/2009 | Dai et al. | |
| 2012/0114765 A1 | 5/2012 | Cao et al. | |

FOREIGN PATENT DOCUMENTS

| | | |
|---|---|---|
| WO | WO-9637465 A1 | 11/1996 |
| WO | WO-2008/008954 A2 | 1/2008 |
| WO | WO-2008/051763 A1 | 5/2008 |
| WO | WO-2010/114881 A1 | 10/2010 |
| WO | WO-2014/172638 A2 | 10/2014 |

OTHER PUBLICATIONS

Romine et al (2004): STN International HCAPLUS database, (Columbus, Ohio), Accession No. 2004:143100.*
International Search Report dated Dec. 8, 2015, from PCT/US2015/041319.
Goodyer et al., "Synthesis of N-benzyl- and N-phenyl-2-amino-4,5-dihydrothiazoles and thioureas and evaluation as modulators of the isoforms of nitric oxide synthase," Bioorganic & Medicinal Chemistry, 11(19):4189-4206 (2003).
Zhang et al., "Development of inhibitors in the ubiquitination cascade," FEBS letters, 588:356-367 (2014).
Baggio et al., "From good substrates to good inhibitors: design of inhibitors for serine and thiol proteases," Biochemistry, 35(11):3351-3353 (1996).
Davies et al., "Constitution of some additive compounds of tertiary phosphines," J Chem Soc, 1786-1792 (1935).
International Search Report dated Nov. 12, 2014, from PCT/US14/34655.
L'Italien et al., "Protein microsequencing with postcolumn fluorescent phenylisothiocyanate analogs," J Chromatog, 283:149-156 (1984).
Smith et al., "Carbohydrate antigens: coupling of oligosaccharide phenethylamine-isothiocyanate derivatives to bovine serum albumin," Methods Enzymol, 50:169-171 (1978).
Basle et al., "Protein Chemical Modification on Endogenous Amino Acids," Chemistry & Biology 17: 213-227 (2010).
Bhattacharya et al., "The principal urinary metabolite of allyl isothiocyanate, N-acetyl-S-(N-allylthiocarbamoyl)cysteine, inhibits the growth and muscle invasion of bladder cancer," Carcinogenesis 33:394-398 (2012).
Chauhan et al., "A small molecule inhibitor of ubiquitin-specific protease-7 induces apoptosis in multiple myeloma cells and overcomes bortezomib resistance," Cancer Cell 22:345-358 (2012).
D'Arcy et al., "Inhibition of proteasome deubiquitinating activity as a new cancer therapy," Nat Med 17:1636-1640 (2011).
Edelmann et al., "Pharmacological targets in the ubiquitin system offer new ways of treating cancer, neurodegenerative disorders and infectious diseases," Expert Rev Mol Med 13:e35 (2011).
Kapuria et al., "Deubiquitinase inhibition by small-molecule WP1130 triggers aggresome formation and tumor cell apoptosis," Cancer research 70:9265-9276 (2010).
Krenn et al., "Inhibition of polyprotein processing and RNA replication of human rhinovirus by pyrrolidine dithiocarbamate involves metal ions," J Virol 79:13892-13899 (2005).
Laine et al., "Inhibitors of cathepsin C (dipeptidyl peptidase I)," Expert Opinion on Therapeutic Patents 20: 497-506 (2010).
Li-Pan et al., "Synthesis and mechanism of action of novel thiocarbamate inhibitors of human leukocyte elastase," J Enzym Inhib 15:63-77 (1999).

(Continued)

*Primary Examiner* — Golam M Shameem
(74) *Attorney, Agent, or Firm* — Foley Hoag LLP

(57) ABSTRACT

Disclosed are small molecule inhibitors of deubiquitinating enzymes (DUBs), and methods of using them. Certain compounds are selective for particular ubiquitin-specific proteases (USPs).

7 Claims, 14 Drawing Sheets

(56) References Cited

OTHER PUBLICATIONS

Lin et al., "Probing structure-function relationships of serine hydrolases and proteases with carbamate and thiocarbamate inhibitors," Protein J 25:33-43 (2006).

Lin et al., "Structure-reactivity relationships for the inhibition mechanism at the second alkyl-chain-binding site of cholesterol esterase and lipase," Biochemistry 38:9971-9981 (1999).

Liu et al., "Discovery of inhibitors that elucidate the role of UCH-L1 activity in the H1299 lung cancer cell line," Chemistry & Biology 10:837-846 (2003).

Matias et al., "Diethyldithiocarbamate induces apoptosis in neuroblastoma cells by raising the intracellular copper level, triggering cytochrome c release and caspase activation," Toxicol in Vitro 27:349-357 (2013).

Matsuno et al., "Diethyldithiocarbamate induces apoptosis in HHV-8-infected primary effusion. lymphoma cells via inhibition of the NF-kappa B pathway," Int J Oncol 40:1071-1078 (2012).

Mattern et al., "Ubiquitin-based anticancer therapy: carpet bombing with proteasome inhibitors vs surgical strikes with E1, E2, E3, or DUB inhibitors," Biochim Biophys Acta 1823:2014-2021 (2012).

Mermerian et al., "Structure-activity relationship, kinetic mechanism, and selectivity for a new class of ubiquitin C-terminal hydrolase-L1 (UCH-L1) inhibitors," Bioorg Med Chem Lett 17:3729-3732 (2007).

Mi et al., "Proteins as binding targets of isothiocyanates in cancer prevention," Carcinogenesis 32(10):1405-1413 (2011).

Mullally et al., "Cyclopentenone prostaglandins of the J series inhibit the ubiquitin isopeptidase activity of the proteasome pathway," The Journal of biological chemistry 276:30366-30373 (2001).

Mullally et al., "Pharmacophore model for novel inhibitors of ubiquitin isopeptidases that induce p53-independent cell death," Mol Pharmacol 62:351-358 (2002).

Nag DK et al., "A small-molecule inhibitor of deubiquitinating enzyme USP14 inhibits Dengue virus replication," Virus Res 165:103-106 (2012).

Nomura et al., "Activity-Based Protein Profiling of Organophosphorus and Thiocarbamate Pesticides Reveals Multiple Serine Hydrolase Targets in Mouse Brain," J Agr Food Chem 59:2808-2815 (2011).

Ratia et al., "A noncovalent class of papain-like protease/deubiquitinase inhibitors blocks SARS virus replication," Proc Natl Acad Sci U S A 105:16119-16124 (2008).

Rawel et al., "Physicochemical and enzymatic properties of benzyl isothiocyanate derivatized proteinases," J Agr Food Chem 46:5043-5051 (1998).

Reverdy et al., "Discovery of specific inhibitors of human USP7/HAUSP deubiquitinating enzyme," Chemistry & Biology 19:467-477 (2012).

Seiberlich et al., "The small molecule inhibitor PR-619 of deubiquitinating enzymes affects the microtubule network and causes protein aggregate formation in neural cells: Implications for neurodegenerative diseases," Bba-Mol Cell Res 1823:2057-2068 (2012).

Tang et al., "Inhibition of Papain by Isothiocyanates," Biochim Biophys Acta 452:510-520 (1976).

* cited by examiner

A)

B)

INHIBITORS OF DEUBIQUITINATING PROTEASES

RELATED APPLICATIONS

This application is the United States National Stage application of PCT/US2015/041319, filed Jul. 21, 2015, which claims the benefit of priority to U.S. patent application Ser. No. 62/027,066, filed Jul. 21, 2014, and 62/067,272, filed Oct. 22, 2014; the contents of each of which are hereby incorporated by reference.

GOVERNMENT SUPPORT

This invention was made with government support under R01-GM100921 awarded by the National Institutes of Health. The government has certain rights in the invention.

BACKGROUND

The ubiquitin system is the linchpin in maintenance of cellular fitness. While many studies have focused on ubiquitylation pathways, comparatively little is known about deubiquitination proteins (DUBs). DUBs are a large group of proteases that regulate ubiquitin-dependent regulatory pathways by cleaving ubiquitin-protein bonds. DUBs can also cleave C-terminally modified ubiquitin. DUBs are also commonly referred to as deubiquitinating proteases, deubiquitylating proteases, deubiquitylating proteinases, deubiquitinating proteinases, deubiquitinating peptidases, deubiquitinating isopeptidases, deubiquitylating isozpeptidases, deubiquitinases, deubiquitylases, ubiquitin proteases, ubiquitin hydrolyases, ubiquitin isopeptidases, or DUBs. The human genome encodes in five gene families nearly 100 DUBs with specificity for ubiquitin. Importantly, DUBs may act as negative and positive regulators of the ubiquitin system. In addition to ubiquitin recycling, they are involved in processing of ubiquitin precursors, in proofreading of protein ubiquitination, and in disassembly of inhibitory ubiquitin chains. The term DUBs also commonly refers to proteases that act on ubiquitin-like proteins such as SUMO, NEDD and ISG15. Such DUBs are also known as deSUMOylases, deNEDDylases and deISGylating.

DUBs play several roles in the ubiquitin pathway. First, DUBs carry out activation of ubiquitin and ubiquitin-like proproteins. Second, DUBs recycle ubiquitin and ubiquitin-like proteins that may have been accidentally trapped by the reaction of small cellular nucleophiles with the thiol ester intermediates involved in the ubiquitination of proteins. Third, DUBs reverse the ubiquitination or ubiquitin-like modification of target proteins. Fourth, DUBs are also responsible for the regeneration of monoubiquitin from unanchored polyubiquitin, i.e., free polyubiquitin that is synthesized de novo by the conjugating cellular machinery or that has been released from target proteins by other DUBs. Finally, the deubiquitinating enzymes UCH-L3 and YUH1 are able to hydrolyse mutant ubiquitin UBB+1 despite the fact that the glycine at position 76 is mutated.

One of the main classes of DUBs is cysteine protease DUBs, examples of which include members of the ubiquitin-specific processing protease (USP/UBP) superfamily, and members of the ubiquitin C-terminal hydrolyase (UCH) superfamily. In humans, these proteases are involved in processes including apoptosis, autophagy, cell cycle, DNA repair, chromosome remodeling, transcription, endocytosis, MHC class II immune responses, cytokine responses, oxidative stress response, angiogenesis, metastasis, prohormone processing, and extracellular matrix remodeling important to bone development. Because the ubiquitin pathways are involved in many important physiological processes, the DUBs are potential targets for the treatment of many diseases, including cancer, inflammation, neurodegeneration, and infection.

Cysteine proteases are potential targets for the treatment of many diseases, including inflammation, spinal cord injury, neurodegeneration, autoimmune diseases, infection, and cancer. A general strategy for the design of cysteine protease inhibitors consists of identification of a "warhead" functionality that reacts with the catalytic cysteine, and recognition elements that target specific inhibitors. Most "warheads" are very reactive functionalities, such as Michael acceptors, epoxides and haloketones, that often react nonspecifically with other proteins. There exists a need for new warheads with lower intrinsic activity and the ability to temporarily modify their targets.

Currently-available cell permeable small molecule inhibitors of DUBs, such as G5 and NSC632839, are reactive compounds that irreversibly modify other proteins in addition to DUBs. Many known DUB inhibitors have two reactive sites that will non-specifically cross-link proteins, causing an accumulation of both high molecular weight ubiquitin species and protein aggregates in in vitro assays. Thus, there exists a need for inhibitors of DUBs or cysteine proteases with reduced intrinsic reactivity.

SUMMARY

In certain embodiments, the invention relates to a compound selected from the group consisting of:

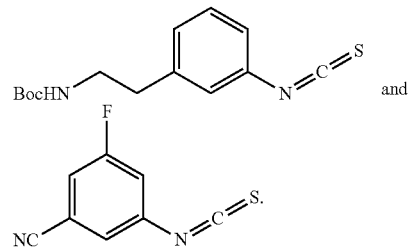

In certain embodiments, the invention relates to a method of inhibiting a deubiquitinating enzyme, comprising the step of: contacting the deubiquitinating enzyme with an effective amount of a compound selected from the group consisting of:

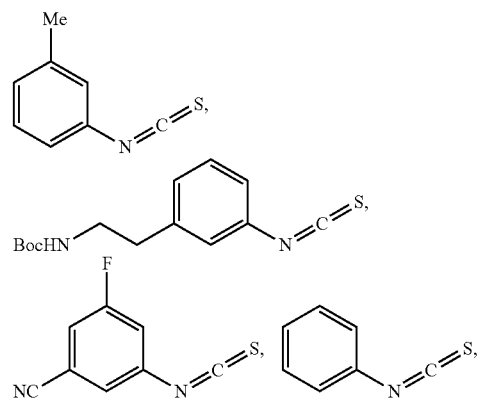

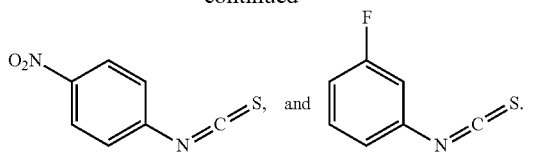

In certain embodiments, the deubiquitinating enzyme is a member of the ubiquitin-specific processing protease (USP/UBP) superfamily or a member of the ubiquitin C-terminal hydrolase (UCHL) superfamily. In certain embodiments, the deubiquitinating enzyme is selected from the group consisting of USP9x, USP7, USP8, USP15, USP27, UCHL5, and UCHL1.

In certain embodiments, the invention relates to a method of preventing or treating a cancer, comprising the step of: administering to a subject in need thereof a therapeutically effective amount of a compound selected from the group consisting of:

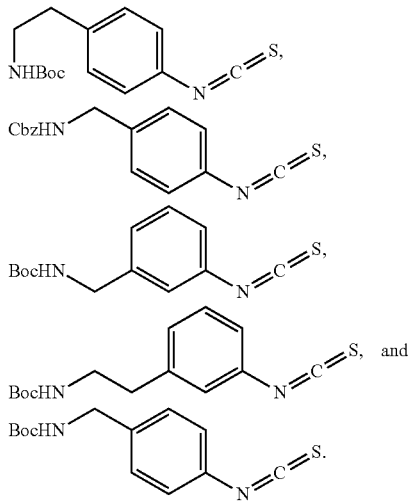

In certain embodiments, the cancer is leukemia, myeloma, lung cancer (e.g., non-small cell lung cancer), colon cancer, central nervous system (CNS) cancer, melanoma, ovarian cancer, renal cancer, prostate cancer, or breast cancer.

In certain embodiments, the invention relates to a method of inhibiting cancer cell growth comprising contacting a cancerous cell with an effective amount of a compound selected from the group consisting of:

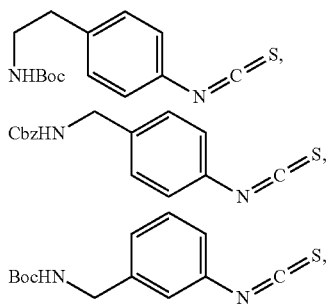

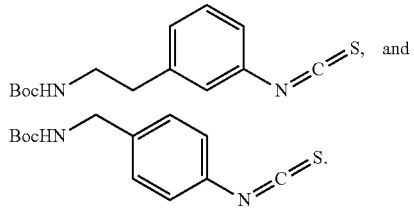

In certain embodiments, the cancerous cell is a human myeloma cell. In certain embodiments, the human myeloma cell is the cell line RPMI 8226.

In certain embodiments, the invention relates to a method of inhibiting a cysteine protease, comprising the step of: contacting the cysteine protease with an effective amount of a compound selected from the group consisting of:

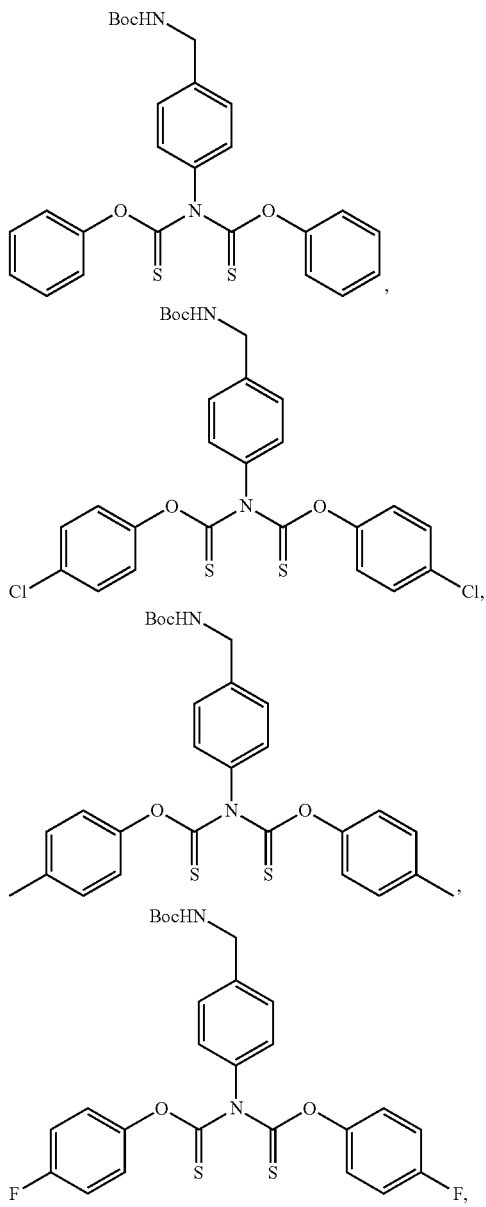

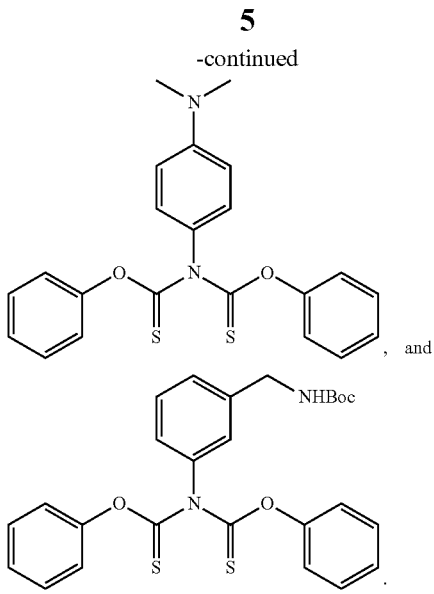

In certain embodiments, the cysteine protease is Cathepsin C.

In certain embodiments, the invention relates to a method of preventing or treating inflammation, comprising the step of: administering to a subject in need thereof a therapeutically effective amount of a compound selected from the group consisting of:

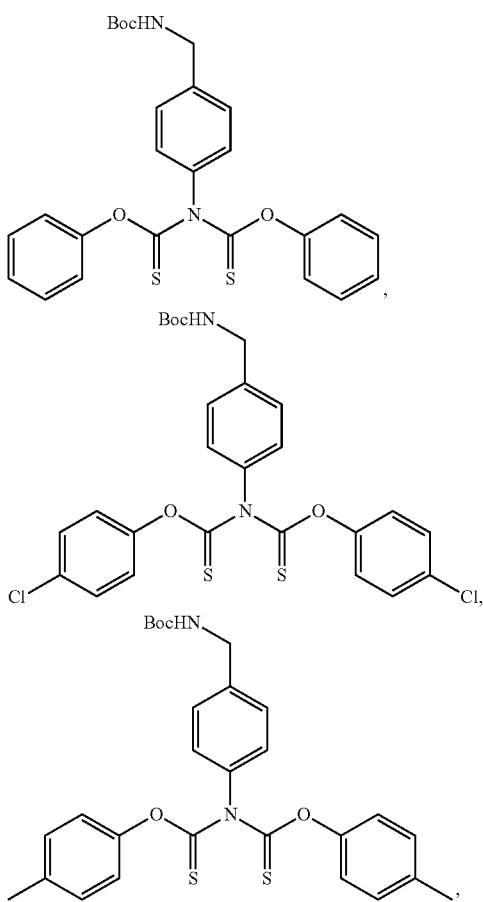

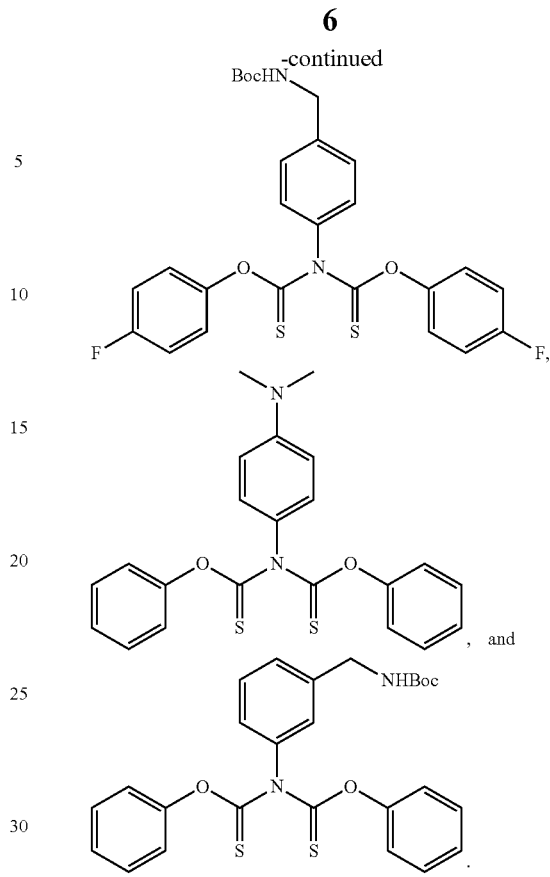

In certain embodiments, the invention relates to the compound:

Figure 1:
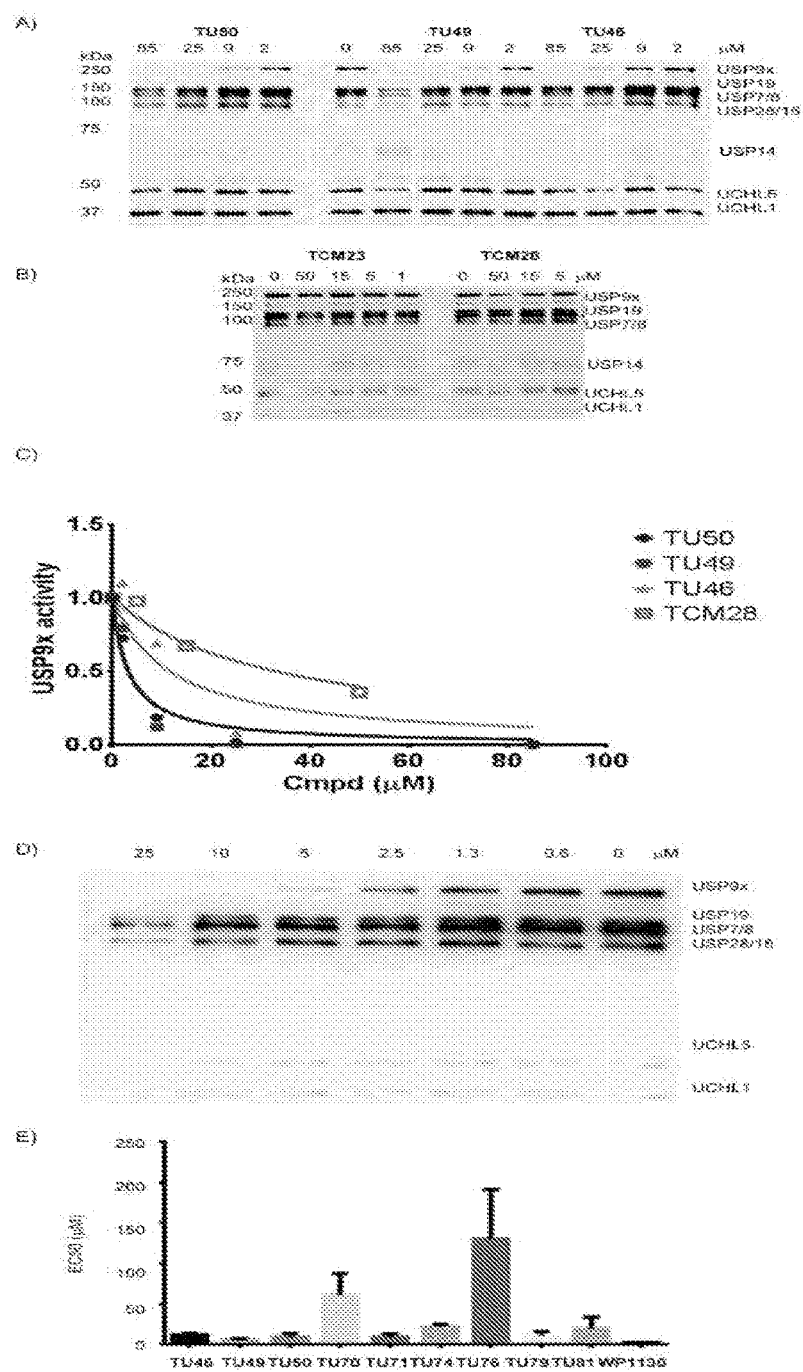
FIG. 1 has five panels (A, B, C, D, and E) depicting data showing that TU compounds are effective inhibitors of USP9x. Panel A is an image of an immunoblot showing the titration of TU50, TU49, TU46 in K562 lysates. Panel B is an image of an immunoblot showing the titration of TCM23 and TCM28 in K562 lysates. Panel C is a plot showing the quantitation of band corresponding to USP9x in panel B. Panel D is an image of an immunoblot showing the titration of WP1130 in K562 lysates. Panel E is a plot showing the quantification of the efficacy of ITCs for the inhibition of USP9x in K562 lysates (see also Table 2).

'Growth percent' is relative to the no drug control and relative to the time zero number of cells. For example, a value of 100 means no growth inhibition and a value of 40 indicates 60% growth inhibition. A value of '0' indicates complete growth inhibition. A negative value indicates 'lethality' and shows that less cells are present after 48 h treatment then at time zero, so, a value of −40 indicates that 40% of the cells have died.

DETAILED DESCRIPTION

Overview

In certain embodiments, the invention relates to compounds comprising a simple, readily modified pharmacophore that inhibits deubiquitination proteins or deubiquitination proteases ("DUBs"). In certain embodiments, the compounds do not comprise a highly reactive electrophile. In certain embodiments, the compounds are selective; that is, the compounds do not significantly or substantially affect the proteasome or caspases. In certain embodiments, the compounds are substantially cell permeable. In certain embodiments, the compounds are effective in a wide range of cell lines.

In certain embodiments, the invention relates to a method of inhibiting a DUB in a cell, comprising contacting the cell with a compound of the invention. In certain embodiments, the methods of the invention result in an accumulation of high molecular weight ubiquitin species. In certain embodiments, the methods of the invention do not result in any substantial accumulation of other protein aggregates.

Because of their mechanism of action, in certain embodiments, these compounds may also inhibit other cysteine proteases, including cathepsin C, caspases, and viral proteases. Cysteine proteases regulate many important physiological processes, and are potential targets for the treatment of many diseases, including inflammation, arthritis, osteoporosis, gingivitis, cancer, neurodegeneration, and infection.

In certain embodiments, treatment of MCF7 cells with a compound of the invention elicits P53 up regulation, which ultimately leads to apoptosis. In certain embodiments, the compounds of the invention also cause degradation of Bcr-Abl kinase and increased monoubiquitination of SMAD4, as expected when USP9x is inhibited. In certain embodiments, the compounds of the invention do not induce the accumulation of insoluble ubiquitin aggregates even at high concentrations.

Definitions

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

In order for the present invention to be more readily understood, certain terms and phrases are defined below and throughout the specification.

The articles "a" and "an" are used herein to refer to one or to more than one (i.e., to at least one) of the grammatical object of the article. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

The term "prodrug" as used herein encompasses compounds that, under physiological conditions, are converted into therapeutically active agents. A common method for making a prodrug is to include selected moieties that are hydrolyzed under physiological conditions to reveal the desired molecule. In other embodiments, the prodrug is converted by an enzymatic activity of the host animal.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material, involved in carrying or transporting the subject chemical from one organ or portion of the body, to another organ or portion of the body. Each carrier must be "acceptable" in the sense of being compatible with the other ingredients of the formulation, not injurious to the patient, and substantially non-pyrogenic. Some examples of materials which can serve as pharmaceutically acceptable carriers include: (1) sugars, such as lactose, glucose, and sucrose; (2) starches, such as corn starch and potato starch; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions of the present invention are non-pyrogenic, i.e., do not induce significant temperature elevations when administered to a patient.

The term "pharmaceutically acceptable salts" refers to the relatively non-toxic, inorganic and organic acid addition salts of the compound(s). These salts can be prepared in situ during the final isolation and purification of the compound(s), or by separately reacting a purified compound(s) in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulfonate salts, and the like. (See, for example, Berge et al. (1977) "Pharmaceutical Salts", *J. Pharm. Sci.* 66:1-19.)

In other cases, the compounds useful in the methods of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of an compound(s). These salts can likewise be prepared in situ during the final isolation and purification of the compound(s), or by separately reacting the purified compound(s) in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

A "therapeutically effective amount" (or "effective amount") of a compound with respect to use in treatment, refers to an amount of the compound in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "patient" refers to a mammal in need of a particular treatment. In certain embodiments, a patient is a primate, canine, feline, or equine. In certain embodiments, a patient is a human.

An aliphatic chain comprises the classes of alkyl, alkenyl and alkynyl defined below. A straight aliphatic chain is limited to unbranched carbon chain moieties. As used herein, the term "aliphatic group" refers to a straight chain, branched-chain, or cyclic aliphatic hydrocarbon group and includes saturated and unsaturated aliphatic groups, such as an alkyl group, an alkenyl group, or an alkynyl group.

"Alkyl" refers to a fully saturated cyclic or acyclic, branched or unbranched carbon chain moiety having the number of carbon atoms specified, or up to 30 carbon atoms if no specification is made. For example, alkyl of 1 to 8 carbon atoms refers to moieties such as methyl, ethyl, propyl, butyl, pentyl, hexyl, heptyl, and octyl, and those moieties which are positional isomers of these moieties. Alkyl of 10 to 30 carbon atoms includes decyl, undecyl, dodecyl, tridecyl, tetradecyl, pentadecyl, hexadecyl, heptadecyl, octadecyl, nonadecyl, eicosyl, heneicosyl, docosyl, tricosyl and tetracosyl. In certain embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer.

"Cycloalkyl" means mono- or bicyclic or bridged saturated carbocyclic rings, each having from 3 to 12 carbon atoms. Likewise, preferred cycloalkyls have from 5-12 carbon atoms in their ring structure, and more preferably have 6-10 carbons in the ring structure.

Unless the number of carbons is otherwise specified, "lower alkyl," as used herein, means an alkyl group, as defined above, but having from one to ten carbons, more preferably from one to six carbon atoms in its backbone structure such as methyl, ethyl, n-propyl, isopropyl, n-butyl, isobutyl, sec-butyl, and tert-butyl. Likewise, "lower alkenyl" and "lower alkynyl" have similar chain lengths. Throughout the application, preferred alkyl groups are lower alkyls. In certain embodiments, a substituent designated herein as alkyl is a lower alkyl.

"Alkenyl" refers to any cyclic or acyclic, branched or unbranched unsaturated carbon chain moiety having the number of carbon atoms specified, or up to 26 carbon atoms if no limitation on the number of carbon atoms is specified; and having one or more double bonds in the moiety. Alkenyl of 6 to 26 carbon atoms is exemplified by hexenyl, heptenyl, octenyl, nonenyl, decenyl, undecenyl, dodenyl, tridecenyl, tetradecenyl, pentadecenyl, hexadecenyl, heptadecenyl, octadecenyl, nonadecenyl, eicosenyl, heneicosoenyl, docosenyl, tricosenyl, and tetracosenyl, in their various isomeric forms, where the unsaturated bond(s) can be located anywhere in the moiety and can have either the (Z) or the (E) configuration about the double bond(s).

"Alkynyl" refers to hydrocarbyl moieties of the scope of alkenyl, but having one or more triple bonds in the moiety.

The term "alkylthio" refers to an alkyl group, as defined above, having a sulfur moiety attached thereto. In certain embodiments, the "alkylthio" moiety is represented by one of —(S)-alkyl, —(S)-alkenyl, —(S)-alkenyl, and —(S)—$(CH_2)_m$—$R^1$, wherein m and $R^1$ are defined below. Representative alkylthio groups include methylthio, ethylthio, and the like.

The terms "alkoxyl" or "alkoxy" as used herein refers to an alkyl group, as defined below, having an oxygen moiety attached thereto. Representative alkoxyl groups include methoxy, ethoxy, propoxy, tert-butoxy, and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R^1$, where m and $R_1$ are described below.

The terms "amine" and "amino" are art-recognized and refer to both unsubstituted and substituted amines, e.g., a moiety that can be represented by the formulae:

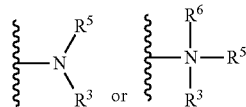

wherein $R^3$, $R^5$ and $R^6$ each independently represent a hydrogen, an alkyl, an alkenyl, —$(CH_2)_m$—$R^1$, or $R^3$ and $R^5$ taken together with the N atom to which they are attached complete a heterocycle having from 4 to 8 atoms in the ring structure; $R^{1R}$ epresents an alkenyl, aryl, cycloalkyl, a cycloalkenyl, a heterocyclyl, or a polycyclyl; and m is zero or an integer in the range of 1 to 8. In certain embodiments, only one of $R^3$ or $R^5$ can be a carbonyl, e.g., $R^3$, $R^5$, and the nitrogen together do not form an imide. In even more certain embodiments, $R^3$ and $R^5$ (and optionally $R^6$) each independently represent a hydrogen, an alkyl, an alkenyl, or —$(CH_2)_m$—$R^1$. Thus, the term "alkylamine" as used herein means an amine group, as defined above, having a substituted or unsubstituted alkyl attached thereto, i.e., at least one of $R_3$ and $R_5$ is an alkyl group. In certain embodiments, an amino group or an alkylamine is basic, meaning it has a conjugate acid with a $pK_a>7.00$, i.e., the protonated forms of these functional groups have $pK_a$s relative to water above about 7.00.

The term "aryl" as used herein includes 3- to 12-membered substituted or unsubstituted single-ring aromatic groups in which each atom of the ring is carbon (i.e., carbocyclic aryl) or where one or more atoms are heteroatoms (i.e., heteroaryl). Preferably, aryl groups include 5- to 12-membered rings, more preferably 6- to 10-membered rings The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Carboycyclic aryl groups include benzene, naphthalene, phenanthrene, phenol, aniline, and the like. Heteroaryl groups include substituted or unsubstituted aromatic 3- to 12-membered ring structures, more preferably 5- to 12-membered rings, more preferably 6- to 10-membered rings, whose ring structures include one to four heteroatoms. Heteroaryl groups include, for example, pyrrole, furan, thiophene, imidazole, oxazole, thiazole, triazole, pyrazole, pyridine, pyrazine, pyridazine and pyrimidine, and the like.

The terms "heterocyclyl" or "heterocyclic group" refer to 3- to 12-membered ring structures, more preferably 5- to 12-membered rings, more preferably 6- to 10-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, sulfamoyl, sulfinyl, ether, alkylthio, sulfonyl, ketone, aldehyde, ester, a heterocyclyl, an aromatic or heteroaromatic moiety, —$CF_3$, —CN, and the like.

The term "carbonyl" is art-recognized and includes such moieties as can be represented by the formula:

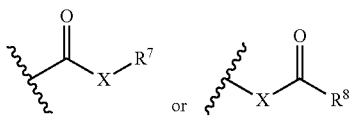

wherein X is a bond or represents an oxygen or a sulfur, and $R^7$ represents a hydrogen, an alkyl, an alkenyl, $-(CH_2)_m-R^1$ or a pharmaceutically acceptable salt, $R^8$ represents a hydrogen, an alkyl, an alkenyl or $-(CH_2)_m-R^1$, where m and $R^1$ are as defined above. Where X is an oxygen and $R^7$ or $R^8$ is not hydrogen, the formula represents an "ester." Where X is an oxygen, and $R^7$ is as defined above, the moiety is referred to herein as a carboxyl group, and particularly when $R^7$ is a hydrogen, the formula represents a "carboxylic acid". Where X is an oxygen, and $R^8$ is a hydrogen, the formula represents a "formate." In general, where the oxygen atom of the above formula is replaced by a sulfur, the formula represents a "thiocarbonyl" group. Where X is a sulfur and $R^7$ or $R^8$ is not hydrogen, the formula represents a "thioester" group. Where X is a sulfur and $R^7$ is a hydrogen, the formula represents a "thiocarboxylic acid" group. Where X is a sulfur and $R^8$ is a hydrogen, the formula represents a "thioformate" group. On the other hand, where X is a bond, and $R^7$ is not hydrogen, the above formula represents a "ketone" group. Where X is a bond, and $R^7$ is a hydrogen, the above formula represents an "aldehyde" group.

The term "thioxamide," as used herein, refers to a moiety that can be represented by the formula:

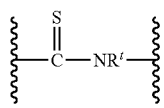

in which $R'$ is selected from the group consisting of the group consisting of hydrogen, alkyl, cycloalkyl, aralkyl, or aryl, preferably hydrogen or alkyl. Moreover, "thioxamide-derived" compounds or "thioxamide analogs" refer to compounds in which one or more amide groups have been replaced by one or more corresponding thioxamide groups. Thioxamides are also referred to in the art as "thioamides."

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "nitro" means $-NO_2$; the term "halogen" designates $-F$, $-Cl$, $-Br$, or $-I$; the term "sulfhydryl" means $-SH$; the term "hydroxyl" means $-OH$; the term "sulfonyl" means $-SO_2-$; the term "azido" means $-N_3$; the term "cyano" means $-CN$; the term "isocyanato" means $-NCO$; the term "thiocyanato" means $-SCN$; the term "isothiocyanato" means $-NCS$; and the term "cyanato" means $-OCN$.

The term "sulfamoyl" is art-recognized and includes a moiety that can be represented by the formula:

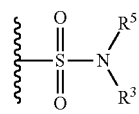

in which $R^3$ and $R^5$ are as defined above.

The term "sulfate" is art recognized and includes a moiety that can be represented by the formula:

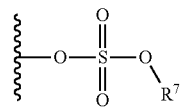

in which $R^7$ is as defined above.

The term "sulfonamide" is art recognized and includes a moiety that can be represented by the formula:

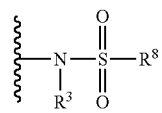

in which $R^3$ and $R^8$ are as defined above.

The term "sulfonate" is art-recognized and includes a moiety that can be represented by the formula:

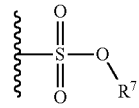

in which $R^7$ is an electron pair, hydrogen, alkyl, cycloalkyl, or aryl.

The terms "sulfoxido" or "sulfinyl", as used herein, refers to a moiety that can be represented by the formula:

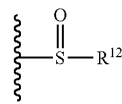

in which $R^{12}$ is selected from the group consisting of the group consisting of hydrogen, alkyl, alkenyl, alkynyl, cycloalkyl, heterocyclyl, aralkyl, or aryl.

The phrase "protecting group", as used herein, means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. Protective Groups in Organic Synthesis, 2nd ed.; Wiley: New York, 1991). Protected forms of the inventive compounds are included within the scope of this invention. For example, "BOC-protected nitrogen," "N—BOC," and "BocHN" refer to a nitrogen atom to which a $(CH_3)_3CO(O)C—$ is covalently bound. Similarly, "BOC-protected compound" refers to an organic compound that comprises a BOC-protected nitrogen.

As used herein, the definition of each expression, e.g., alkyl, m, n, etc., when it occurs more than once in any structure, is intended to be independent of its definition elsewhere in the same structure.

For purposes of this invention, the chemical elements are identified in accordance with the Periodic Table of the Elements, CAS version, Handbook of Chemistry and Physics, 67th Ed., 1986-87, inside cover.

Exemplary Compounds

In certain embodiments, the invention relates to a compound selected from the group consisting of:

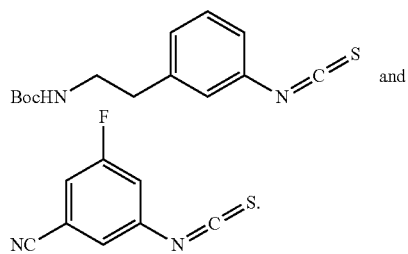

In certain embodiments, the invention relates to any one of the aforementioned compounds, wherein the compound is a pharmaceutically acceptable salt.

In certain embodiments, the invention relates to the compound:

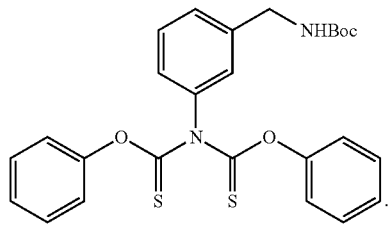 [SMILES: CC(C)(C)OC(=O)NCc1cccc(N(C(=S)Oc2ccccc2)C(=S)Oc2ccccc2)c1]

In certain embodiments, the invention relates to any one of the aforementioned compounds, wherein the compound is a pharmaceutically acceptable salt.

Exemplary Pharmaceutical Compositions

In certain embodiments, the invention relates to a pharmaceutical composition comprising any one of the aforementioned compounds and a pharmaceutically acceptable carrier.

Patients, including but not limited to humans, can be treated by administering to the patient an effective amount of the active compound or a pharmaceutically acceptable prodrug or salt thereof in the presence of a pharmaceutically acceptable carrier or diluent. The active materials can be administered by any appropriate route, for example, orally, parenterally, intravenously, intradermally, subcutaneously, or topically, in liquid or solid form.

In certain embodiments, a dose of the compound will be in the range of about 0.1 to about 100 mg/kg, more generally, about 1 to 50 mg/kg, and, preferably, about 1 to about 20 mg/kg, of body weight of the recipient per day. The effective dosage range of the pharmaceutically acceptable salts and prodrugs can be calculated based on the weight of the parent compound to be delivered. If the salt or prodrug exhibits activity in itself, the effective dosage can be estimated as above using the weight of the salt or prodrug, or by other means known to those skilled in the art.

The compound is conveniently administered in unit any suitable dosage form, including but not limited to one containing 7 to 3,000 mg, preferably 70 to 1400 mg of active ingredient per unit dosage form. An oral dosage of 50-1,000 mg is usually convenient.

Ideally the active ingredient should be administered to achieve peak plasma concentrations of the active compound from about 0.2 to 70 μM, preferably about 1.0 to 15 μM. This can be achieved, for example, by the intravenous injection of a 0.1 to 5% solution of the active ingredient, optionally in saline, or administered as a bolus of the active ingredient.

The concentration of active compound in the drug composition will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient can be administered at once, or can be divided into a number of smaller doses to be administered at varying intervals of time.

In certain embodiments, the mode of administration of the active compound is oral. Oral compositions will generally include an inert diluent or an edible carrier. They can be enclosed in gelatin capsules or compressed into tablets. For the purpose of oral therapeutic administration, the active compound can be incorporated with excipients and used in the form of tablets, troches or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, unit dosage forms can contain various other materials that modify the physical form of the dosage unit, for example, coatings of sugar, shellac, or other enteric agents.

The compound can be administered as a component of an elixir, suspension, syrup, wafer, chewing gum or the like. A syrup can contain, in addition to the active compound(s), sucrose or sweetener as a sweetening agent and certain preservatives, dyes and colorings and flavors.

The compound or a pharmaceutically acceptable prodrug or salts thereof can also be mixed with other active materials that do not impair the desired action, or with materials that supplement the desired action, such as antibiotics, antifungals, anti-inflammatories or other antivirals, including but not limited to nucleoside compounds. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents, such as ethylenediaminetetraacetic acid; buffers, such as acetates, citrates or phosphates, and agents for the adjustment of tonicity, such as sodium chloride or dextrose. The parental preparation can be enclosed in ampoules, disposable syringes or multiple dose vials made of glass or plastic.

If administered intravenously, carriers include physiological saline and phosphate buffered saline (PBS).

In certain embodiments, the active compounds are prepared with carriers that will protect the compound against rapid elimination from the body, such as a controlled release formulation, including but not limited to implants and microencapsulated delivery systems. Biodegradable, biocompatible polymers can be used, such as ethylene vinyl acetate, polyanhydrides, polyglycolic acid, collagen, polyorthoesters and polylactic acid. For example, enterically coated compounds can be used to protect cleavage by stomach acid. Methods for preparation of such formulations will be apparent to those skilled in the art. Suitable materials can also be obtained commercially.

Liposomal suspensions (including but not limited to liposomes targeted to infected cells with monoclonal antibodies to viral antigens) are also preferred as pharmaceutically acceptable carriers. These can be prepared according to methods known to those skilled in the art, for example, as described in U.S. Pat. No. 4,522,811 (incorporated by reference). For example, liposome formulations can be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound is then introduced into the container. The container is then swirled by hand to free lipid material from the sides of the container and to disperse lipid aggregates, thereby forming the liposomal suspension.

Exemplary Methods

In certain embodiments, the invention relates to a method of preventing or treating a disease in a subject in need thereof, comprising the step of: administering to the subject a therapeutically effective amount of any one of the aforementioned compounds.

In certain embodiments, the invention relates to a method of preventing or treating a disease in a subject in need thereof, comprising the step of: administering to the subject a therapeutically effective amount of a compound selected from the group consisting of:

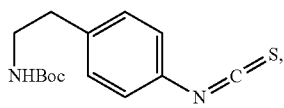

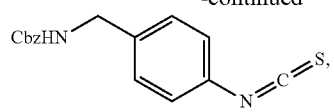

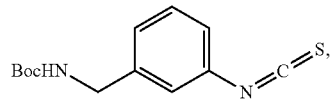 [SMILES: CC(C)(C)OC(=O)NCc1cccc(N=C=S)c1]

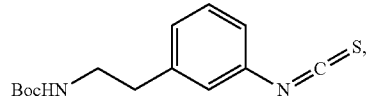

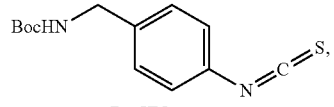

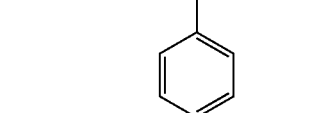

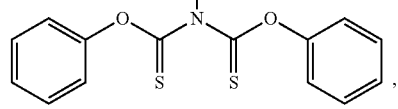

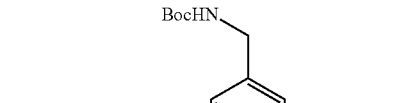

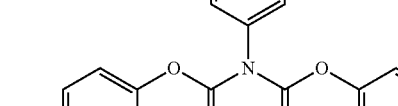

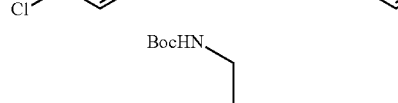

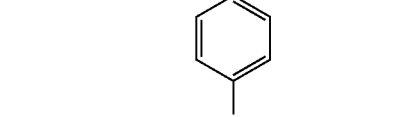

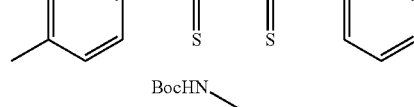

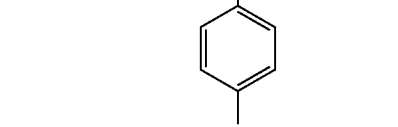

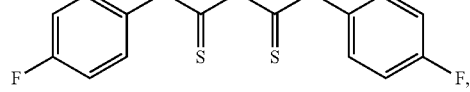

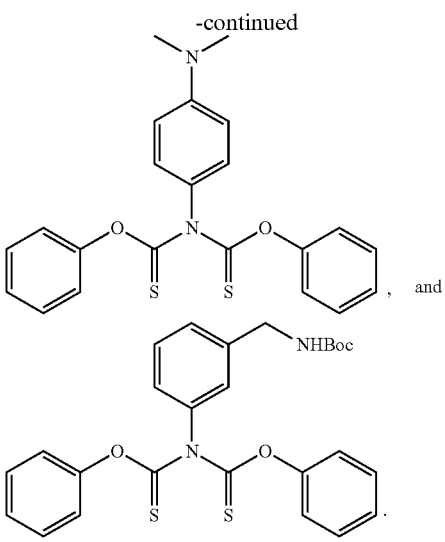
, and

In certain embodiments, the invention relates to any one of the aforementioned methods, wherein the disease is a proteinopathy. Examples of such proteinopathies include, but are not limited to, Alzheimer's disease, cerebral β-amyloid angiopathy, retinal ganglion cell degeneration, prion diseases (e.g., bovine spongiform encephalopathy, kuru, Creutzfeldt-Jakob disease, variant Creutzfeldt-Jakob disease, Gerstmann-Straussler-Scheinker syndrome, fatal familial insomnia) tauopathies (e.g., frontotemporal dementia, Parkinson's disease, progressive supranuclear palsy, corticobasal degeneration, frontotemporal lobar degeneration), frontotemporal lobar degeneration, amyotrophic lateral sclerosis, Huntington's disease, familial British dementia, Familial Danish dementia, hereditary cerebral hemorrhage with amyloidosis (Icelandic), CADASIL, Alexander disease, Seipinopathies, familial amyloidotic neuropathy, senile systemic amyloidosis, serpinopathies, AL amyloidosis, AA amyloidosis, type II diabetes, aortic medial amyloidosis, ApoAI amyloidosis, ApoAII amyloidosis, ApoAIV amyloidosis, familial amyloidosis of the Finish type, lysozyme amyloidosis, fibrinogen amyloidosis, dialysis amyloidosis, inclusion body myositis/myopathy, cataracts, medullary thyroid carcinoma, cardiac atrial amyloidosis, pituitary prolactinoma, hereditary lattice corneal dystrophy, cutaneous lichen amyloidosis, corneal lactoferrin amyloidosis, corneal lactoferrin amyloidosis, pulmonary alveolar proteinosis, odontogenic tumor amylosis, seminal vesical amyloid, cystic fibrosis, sickle cell disease, critical illness myopathy, von Hippel-Lindau disease, spinocerebellar ataxia 1, Angelman syndrome, giant axon neuropathy, inclusion body myopathy with Paget disease of bone, and frontotemporal dementia (IBMPFD).

In certain embodiments, the invention relates to any one of the aforementioned methods, wherein the disease is a cell proliferative disorder or disease. In certain embodiments, the disease is cancer, tumor, neoplasm, neovascularization, vascularization, cardiovascular disease, intravasation, extravasation, metastasis, arthritis, infection, blood clot, atherosclerosis, melanoma, skin disorder, rheumatoid arthritis, diabetic retinopathy, macular edema, or macular degeneration, inflammatory and arthritic disease, autoimmune disease or osteosarcoma. Certain therapeutic methods of the invention include treating malignancies, including solid tumors and disseminated cancers. Exemplary tumors that may be treated in accordance with the invention include e.g., cancers of the lung, prostate, breast, liver, colon, breast, kidney, pancreas, brain, skin including malignant melanoma and Kaposi's sarcoma, testes or ovaries, or leukemias or lymphoma including Hodgkin's disease. Exemplary autoimmune diseases include, but are not limited to lupus.

In certain embodiments, the cancer is leukemia (e.g., acute lymphoblastic leukemia (adult or childhood), acute myeloid leukemia (adult or childhood), chronic lymphocytic leukemia, chronic myelogenous leukemia, hairy cell leukemia), myeloma (e.g., multiple myeloma), lung cancer (e.g., non-small cell lung cancer), colon cancer, central nervous system (CNS) cancer, melanoma, ovarian cancer, renal cancer, prostate cancer, or breast cancer. In certain embodiments, the cancer is a leukemia.

In certain embodiments, the invention relates to any one of the aforementioned methods, wherein the disease is an infection.

In certain embodiments, the invention relates to any one of the aforementioned methods, wherein the infection is a protozoan, helminthic, fungal, bacterial, or viral infection.

In certain embodiments, the invention relates to any one of the aforementioned methods, wherein the infection is malaria, toxoplasmosis, schistosomaisis, a trypanosomal parasitic infection, Chagas' disease, leishmaniasis, or human African trypanosomiasis.

In certain embodiments, the invention relates to any one of the aforementioned methods, wherein the infection is an *Entamoeba histolytica* infection or a *Giardia* infection.

In certain embodiments, the invention relates to any one of the aforementioned methods, wherein the infection is an *Opisthorchis viverrini* infection, a *Clonorchis sinensis* infection, an *Angiostrongylus cantonensis* infection, an *Angiostrongylus cantonensis* infection, a *Fasciola hepatica* infection, a *Fasciola gigantica* infection, a *Dictyocaulus viviparous* infection, a *Haemonchus contortus* infection, or a *Schistosoma* infection.

In certain embodiments, the invention relates to any one of the aforementioned methods, wherein the infection is a *Cryptococcus neoformans* infection.

In certain embodiments, the invention relates to any one of the aforementioned methods, wherein the infection is a SARS infection, a Picornaviral infection, a Coronaviral infection, a Epstein Barr infection, an arterivirus or a nairovirus infection, a Kaposi's sarcoma-associated herpesvirus infection, a foot-and-mouth disease virus infection, a Crimean Congo hemorrhagic fever virus (CCHFV) infection, a Hepatitis B virus infection, or a human cytomegalovirus infection.

In certain embodiments, the invention relates to any one of the aforementioned methods, wherein the infection is a *Staphylococcus aureus* infection, *Porphyromonas gingivalis* infection, a *Yersinia pestis* infection, a *Salmonella* infection, a *Chlamydia* infection, or a *Clostridium difficile* infection.

In certain embodiments, the invention relates to any one of the aforementioned methods, wherein the subject is a mammal. In certain embodiments, the invention relates to any one of the aforementioned methods, wherein the subject is human.

In certain embodiments, the invention relates to a method of inhibiting a cysteine protease, comprising the step of: contacting the cysteine protease with an effective amount of any one of the aforementioned compounds.

In certain embodiments, the invention relates to a method of inhibiting a cysteine protease, comprising the step of: contacting the cysteine protease with an effective amount of a compound selected from the group consisting of:

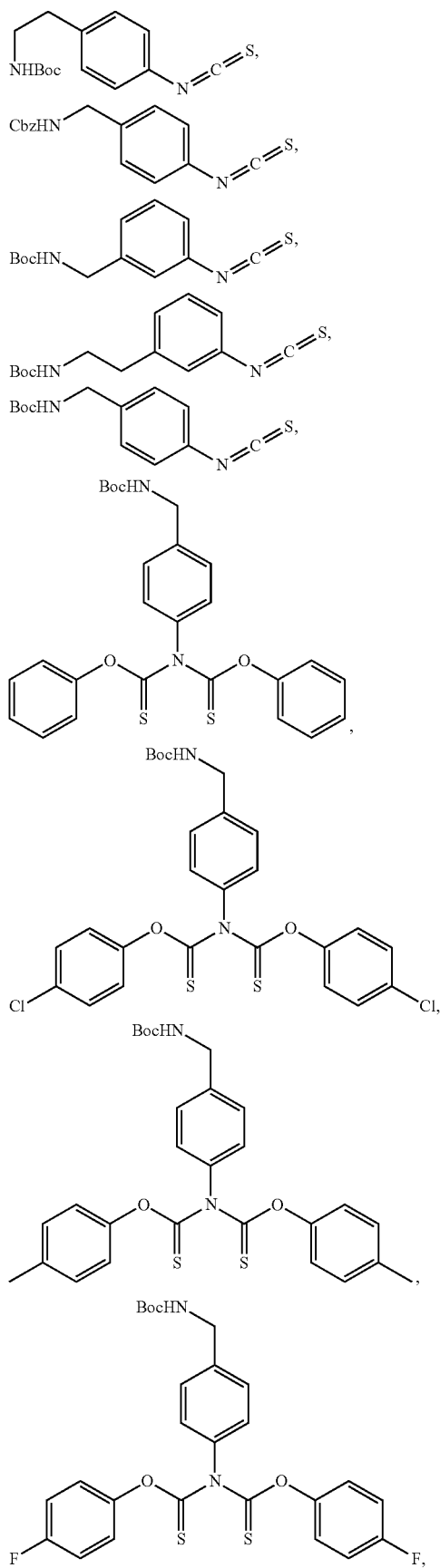

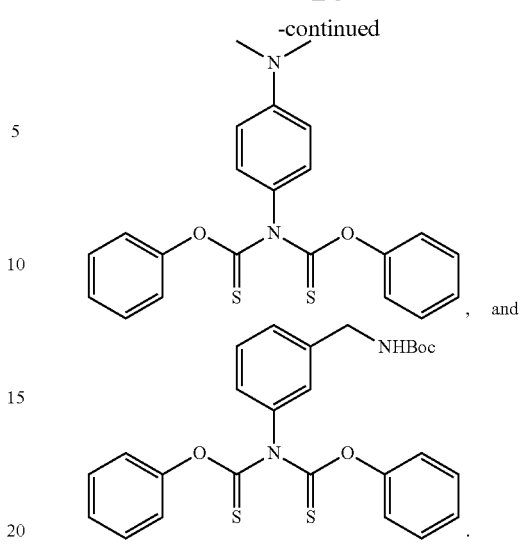

In certain embodiments, the invention relates to any one of the aforementioned methods, wherein the cysteine protease is cathepsin. In certain embodiments, the invention relates to any one of the aforementioned methods, wherein the cysteine protease is cathepsin C. In general, cathepsins are involved in inflammatory or autoimmune diseases such as atherosclerosis, obesity, rheumatoid arthritis, cardiac repair, cardiomyopathy, and cancer.

In certain embodiments, the invention relates to any one of the aforementioned methods, wherein the cysteine protease is a MALT1 protease.

In certain embodiments, the invention relates to any one of the aforementioned methods, wherein the cysteine protease is a caspase or a calpain. Caspases are involved in cancer, inflammation, and neurodegeneration. Calpains are involved in necrosis, ischemia and reperfusion injury, neurological disorders, muscular dystrophies, cataract, cancer, diabetes, gastropathy, Alzheimer's disease, Parkinson's disease, atherosclerosis, and pulmonary hypertension.

In certain embodiments, the invention relates to any one of the aforementioned methods, wherein the cysteine protease is falcipain, cruzain, Leishmania CPA protease, Leishmania CPB protease, Leishmania CPS protease, an *Entamoeba histolytica* cysteine protease (e.g., EhCP1, EhCP2, or EhCP3), or a *Giardia* cysteine protease.

In certain embodiments, the invention relates to any one of the aforementioned methods, wherein the cysteine protease is an *Opisthorchis viverrini* cysteine protease, a *Clonorchis sinensis* cysteine protease, an *Angiostrongylus cantonensis* cathepsin B-like enzyme gene 1, 2 (e.g., AC-cathB-1, AC-cathB-2), an *Angiostrongylus cantonensis* hemoglobin-type cysteine protease, a *Fasciola hepatica* virulence-associated cysteine peptidase, a *Fasciola gigantica* protein, a bovine lungworm *Dictyocaulus viviparous* cysteine protease, a *Haemonchus contortus* cysteine protease, or a *Schistosoma* cysteine protease.

In certain embodiments, the invention relates to any one of the aforementioned methods, wherein the cysteine protease is *Cryptococcus neoformans* Ubp5.

In certain embodiments, the invention relates to any one of the aforementioned methods, wherein the cysteine protease is a SARS PL protease, a Picornaviral 3C protease, a Coronaviral 3C-like protease, a Epstein Barr virus deubiquitinating protease, an arterivirus or a nairovirus ovarian tumor domain-containing deubiquitinase, a Kaposi's sarcoma-associated herpesvirus-encoded deubiquitinase (e.g., ORF64), a foot-and-mouth disease virus (FMDV) papain-like proteinase, a Crimean Congo hemorrhagic fever virus (CCHFV) deubiquitinase, a Hepatitis B virus protein X, or a human cytomegalovirus high-molecular-weight protein (e.g., HMWP or pUL48)

In certain embodiments, the invention relates to any one of the aforementioned methods, wherein the cysteine protease is a Sortase transpeptidase from a Gram positive bacterium (e.g., *Staphylococcus aureus*), gingipain (e.g., from *Porphyromonas gingivalis*), a *Yersinia pestis* virulence factor (e.g., YopJ), an ElaD ortholog (e.g., *Salmonella* sseL), *Chlamydia* DUB1 or DUB2, *Streptococcus pyogenes* SpeB, *Clostridium difficile* Cwp84 or Cwp13 cysteine protease, toxin TcdA, or toxin TcdB.

In certain embodiments, the invention relates to any one of the aforementioned methods, wherein the cysteine protease is a deSUMOylase, a deNEDDylase, or a deISGylase.

In certain embodiments, the invention relates to any one of the aforementioned methods, wherein the compound is selective for the cysteine protease.

In certain embodiments, the invention relates to any one of the aforementioned methods, wherein the compound is specific for the cysteine protease.

In certain embodiments, the invention relates to any one of the aforementioned methods, wherein the cysteine protease is in vitro or in vivo.

In certain embodiments, the invention relates to any one of the aforementioned methods, wherein the compound is substantially cell permeable.

In certain embodiments, the invention relates to a method of inhibiting a deubiquitinating enzyme comprising the step of: contacting the deubiquitinating enzyme with an effective amount of any one of the aforementioned compounds.

In certain embodiments, the invention relates to a method of inhibiting a deubiquitinating enzyme, comprising the step of: contacting the deubiquitinating enzyme with an effective amount of a compound selected from the group consisting of:

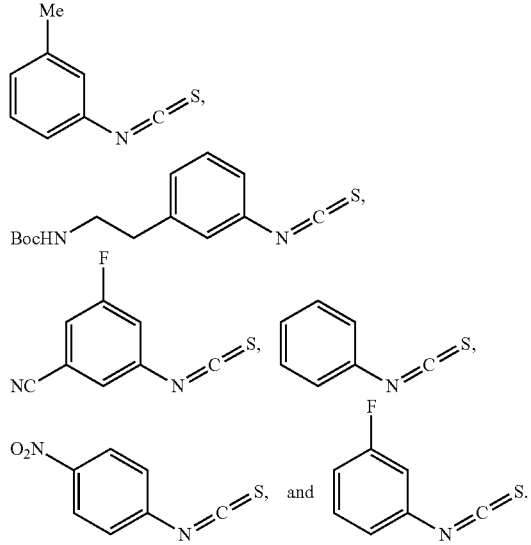

In certain embodiments, the invention relates to any one of the aforementioned methods, wherein the compound is selective for the deubiquitinating enzyme.

In certain embodiments, the invention relates to any one of the aforementioned methods, wherein the compound is specific for the deubiquitinating enzyme.

In certain embodiments, the invention relates to any one of the aforementioned methods, wherein the deubiquitinating enzyme is a member of the ubiquitin-specific processing protease (USP/UBP) superfamily or a member of the ubiquitin C-terminal hydrolyase (UCH) superfamily. In certain embodiments, the invention relates to any one of the aforementioned methods, wherein the deubiquitinating enzyme is selected from the group consisting of: USP9x, USP5, USP7, USP14, UCH37, and UCHL3. In certain embodiments, the invention relates to any one of the aforementioned methods, wherein the deubiquitinating enzyme is USP9x.

In certain embodiments, the invention relates to any one of the aforementioned methods, wherein the deubiquitinating enzyme is in vitro or in vivo.

In certain embodiments, the invention relates to any one of the aforementioned methods, wherein the compound is substantially cell permeable.

EXEMPLIFICATION

The invention now being generally described, it will be more readily understood by reference to the following examples, which are included merely for purposes of illustration of certain aspects and embodiments of the present invention, and are not intended to limit the invention.

EXAMPLE 1—Compounds

TABLE 1

| Structure | Compound |
|---|---|
| BocHN—⟨⟩—NH—C(=S)—O—⟨⟩ | TCM23 |
| BocHN—⟨⟩—NH—C(=S)—O—⟨⟩—Cl | TCM28 |
| BocHN—⟨⟩—N(C(=S)—O—⟨⟩)(C(=S)—O—⟨⟩) | TCM41 |

TABLE 1-continued

| Structure | Compound |
|---|---|
| (BocHN-CH2-C6H4-N(C(=S)O-C6H4-Cl)2) | TCM40 |
| (BocHN-CH2-C6H4-N(C(=S)O-C6H4-Me)2) | TCM42 |
| (BocHN-CH2-C6H4-N(C(=S)O-C6H4-F)2) | TCM58 |
| (Me2N-C6H4-N(C(=S)O-Ph)2) | TCM43 |
| (BocHN-CH2-C6H4(m)-N(C(=S)O-Ph)2) | TCM97 |
| (H2N-CH2-C6H4-NCS) | TU45 |

TABLE 1-continued

| Structure | Compound |
|---|---|
| BocHN-CH2CH2-C6H4-NCS (para) | TU46 |
| CbzHN-CH2-C6H4-NCS (para) | TU49 |
| BocHN-CH2-C6H4-NCS (meta) | TU50 |
| 3-Me-C6H4-NCS | TU70 |
| BocHN-CH2CH2-C6H4-NCS (meta) | TU71 |
| 3-F-5-CN-C6H3-NCS | TU74 |
| C6H5-NCS | TU76 |
| 4-O2N-C6H4-NCS | TU79 |
| 3-F-C6H4-NCS | TU81 |

EXAMPLE 2—Synthesis of Compounds

All reactions were carried out under an atmosphere of dry nitrogen supplied by balloon. All solvents and amine bases were either distilled before use or bought dry over molecular sieves. All aqueous solutions were saturated unless otherwise stated.

Scheme 1

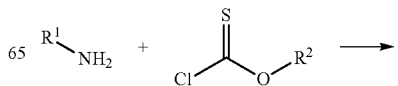

-continued

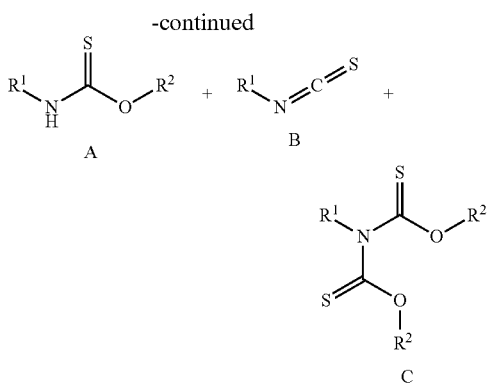

General Procedure 1.

To the amine in pyridine and DMF (1:1) over molecular sieves (4 Å) at 4° C. was added the chloro thionoformate drop-wise (vigorous stirring is recommended at this juncture to avoid clogging due to precipitation of HCl salts). The mixture became orange and was stirred overnight at 4° C. After this time EtOAc was added. This mixture was extracted sequentially with sodium bicarbonate, copper sulfate (2-3 times) then water 3 times, then brine. The organic phase was dried with magnesium sulfate, filtered and concentrated at low temperature to yield the crude mixture typically as an orange gum. This procedure gave 3 main products, the isothiocyanate (which was always the same product irrespective of the chloro thionoformate starting material, provided the amine was constant), the dual adduct (e.g., TCM41, all were bright yellow solids) and the thiocarbamate which eluted in that order on silica gel. See Scheme 1.

General Procedure 2.

To a round bottom flask was added molecular sieves and a stir bar and the flask was heated to dryness over a Bunsen flame, then cooled over vacuum for 20 min. The amine was added to the flask, then a stopper was added and the flask flushed with dry nitrogen. DMF/pyridine (1:1) was then added and the flask cooled to 4° C. The chloroformate was then added drop-wise (neat if liquid or as a solution in DMF, if solid). After 1 h the reaction was warmed to rt and run overnight. After this time $NaHCO_3$ and EtOAc was added and the reaction stirred for 5 min. The aqueous phase was extracted, then the organic phase was washed 3 times with 10% $CuSO_4$, three times with water, then once with brine. Organic phase was then dried with magnesium sulfate, filtered and concentrated.

General Procedure 3.

The Boc protected compound was added to a dry flask, then 2 M $HCl.Et_2O$ with 10% DMF was added. Mixture was stirred overnight after which time a solid formed. The solid was filtered, washed 3 times with $Et_2O$ then concentrated in vacuo General procedure 3. A carboxylic acid, alcohol, EDCI and $Et_3N$ were stirred overnight in DMF. After this time reaction was diluted with EtOAc, and water was added. This mixture was stirred for 5 min, then phases were separated and the organic phase was washed three times with water, and once with brine. The organic phase was dried with magnesium sulfate, filtered and concentrated.

Synthesis of TCM23

Following General Procedure 1, phenylchloro thionoformate (0.72 mg, 4.2 mmol), N-Boc 4-methylamino aniline (1.0 g, 4.2 mmol), pyridine (20 mL), DMF (20 mL). Purification by chromatography on silica (2% EtOAc to 100% EtOAc) yielded the title compound as an off white solid (300 mg, 20%). δH (400 mHz, $CDCl_3$) 1.437 (9H, s), 4.281 (2H, s), 7.120 (2H, d, J=8.4 Hz), 7.274-7.292 (4H, m), 7.314 (2H, d, J=8.2 Hz). m/z ESI+359 (MH+).

Synthesis of TCM29

Following General Procedure 1, phenylchloro thionoformate (0.72 mg, 4.2 mmol), N-Boc 4-methylamino aniline (1 g, 4.2 mmol), pyridine (20 mL), DMF (20 mL). Purification by chromatography on silica (2% EtOAc to 100% EtOAc) yielded the title compound as an off white solid (100 mg, 9%). δH (400 mHz, DMSO-D6) 1.346 (9H, s), 4.086 (2H, d, J=6.0 Hz), 7.248 (2H, d, J=8.0 Hz), 7.338 (2H, d, J=7.8 Hz), 7.389 (1H, s). δC (100 mHz, DMSO-D6) 31.312, 46.000, 81.037, 128.915, 131.372, 131.410, 136.201, 143.434, 158.870. m/z EI 264 (M+) 207 M-$C(CH_3)_3$.

Synthesis of TCM40

Following General Procedure 1, 4-chlorophenylchloro thionoformate (0.864 mg, 4.2 mmol), N-Boc 4-methylamino aniline (1 g, 4.2 mmol), pyridine (20 mL), DMF (20 mL). Purification by chromatography on silica (2% EtOAc to 100% EtOAc) yielded the title compound as a yellow solid (200 mg, 10%). δH (400 mHz, DMSO-D6) 1.357 (9H, s), 4.146 (2H, d, J=5.2 Hz), 7.250 (4H, d, J=7.6 Hz), 7.325 (2H, d, J=7.6 Hz), 7.410 (1H, m), 7.523 (6H, m). δC (100 mHz, DMSO-D6) 31.535, 46.515, 81.044, 126.709, 130.646, 131.135, 133.027, 134.255, 144.342, 155.077, 193.067.

Synthesis of TCM41

Following General Procedure 1, phenylchloro thionoformate (0.725 mg, 4.2 mmol), N-Boc 4-methylamino aniline (1 g, 4.2 mmol), pyridine (20 mL), DMF (20 mL). Purification by chromatography on silica (2% EtOAc to 100% EtOAc) yielded the title compound as a yellow solid (103 mg, 5%). δH (400 mHz, DMSO-D6) 1.447 (9H, s), 4.357 (2H, d, J=4.4 Hz), 4.821 (1H, s), 7.151 (4H, d, J=8.0 Hz), 7.325 (2H, d, J=7.6 Hz), 7.410 (1H, m), 7.523 (6H, m). δC (100 mHz, DMSO-D6) 31.037, 46.847, 82.357, 124.391, 129.381, 130.853, 131.326, 132.311, 145.043, 156.460, 193.267. m/z EI 494 M+, 393 M− Boc+.

Synthesis of TCM42

Following General Procedure 1, p-tolylchloro thionoformate (0.7 mL, 4.2 mmol), N-Boc 4-methylamino aniline (1 g, 4.2 mmol), pyridine (20 mL), DMF (20 mL). Purification by chromatography on silica (2% EtOAc to 100% EtOAc) yielded the title compound as a yellow solid (329 mg, 15%). δH (400 mHz, DMSO-D6) 1.360 (9H, s), 2.270 (6H, s), 4.140 (2H, d, J=5.2 Hz), 7.054 (4H, d, J=8.4 Hz), 7.2226 (4H, d, J=8.4 Hz), 7.315 (2H, d, J=8.4 Hz), 7.400 (1H, s), 7.501 (2H, d, J=8.8 Hz). δC (100 mHz, DMSO-D6) 23.537, 31.350, 46.015, 81.029, 124.260, 130.708, 131.104, 133.340, 139.261, 143.969, 144.533, 154.414, 158.961, 193.792. ESI+ 523 MH+.

Synthesis of TCM43

Following General Procedure 1, phenylchloro thionoformate (0.7 g, 4.2 mmol), N,N-dimethylamino aniline (1 g, 7.4 mmol), pyridine (20 mL), DMF (20 mL). Purification by chromatography on silica (2% EtOAc to 100% EtOAc) yielded the title compound as a yellow solid (221 mg, 15%). δH (400 mHz, DMSO-D6) 3.184 (6H, s), 7.141 (4H, d, J=8.0 Hz), 7.291 (2H, t, J=8.0 Hz), 7.415 (4H, t, J=7.8 Hz), 7.648 (2H, d, J=7.9 Hz), 7.835 (2H, d, J=7.9 Hz). δC (100 mHz, DMSO-D6) 40.605, 124.642, 129.960, 131.990, 133.050, 156.512, 193.502. m/z EI 264 (M+).

Synthesis of TU45

TCM29 (50 mg, 0.2 mmol) was dissolved in 4 M HCl in $Et_2O$ and stirred overnight. The solid was filtered off and washed with Et2O three times to give the pure compound as a white solid (15 mg, 50%). δH (400 mHz, DMSO-D6) 3.980 (2H, s), 7.425 (2H, d, J=8.0 Hz), 7.556 (2H, d, J=8.0

Hz), 8.627 (3H, s). δC (100 mHz, DMSO-D6) 44.558, 129.096, 133.096, 133.660, 136.858, 137.079. m/z CI 164 (100% M+).

Synthesis of TU46

Following General Procedure 1, p-tolyl chlorothionoformate (0.7 mL, 4.2 mmol), [2-(4-aminophenyl)ethyl]carbamic acid tert butyl (1 g, 4.2 mmol), pyridine (20 mL), DMF (20 mL). Purification by chromatography on silica (2% EtOAc to 100% EtOAc) yielded the title compound as a white solid (151 mg, 12%). δH (400 mHz, DMSO-D6) 1.308 (9H, s), 2.661 (2H, t, J=6.8 Hz), 3.083 (2H, q, J=6.8 Hz), 6.800 (1H, s), 7.216 (2H, d, J=7.6 Hz), 7.304 (2H, d, J=7.6 Hz). δC (100 mHz, DMSO-D6) 31.320, 38.095, 44.191, 80.617, 128.869, 130.914, 133.218, 136.056, 142.893, 158.588. m/z 278 MH+. HREIMS found 279.1167 C14H19N2O2S, requires 279.1167.

For large scale preps: [2-(4-aminophenyl)ethyl]carbamic acid tert butyl (1 g, 4.2 mmol), DCM (20 mL) and triethyl amine (0.6 mL) in a round bottom flask that had been flame dried in the presence of molecular sieves and cooled under vacuum was stirred at 4° C. After 10 min di 2-pyridyl thionocarbonate (1 g, 4.2 mmol) was added. The reaction was stirred overnight at 4° C. after which time the DCM layer was washed twice with water and once with brine. Chromatography on silica gel yielded the titled compound (0.7 g, 60%) as a white solid with identical 1H NMR spectra to those above.

Synthesis of TU49

Following General Procedure 1, phenyl chlorothionoformate (0.7 mL, 4.2 mmol), N-Cbz 4-aminomethyl aniline (1.1 g, 4.2 mmol), pyridine (20 mL), DMF (20 mL). Purification by chromatography on silica (2% EtOAc to 100% EtOAc) yielded the title compound as a white solid (200 mg, 15%). δH (400 mHz, DMSO-D6) 4.174 (2H, d, J=6.4 Hz), 5.000 (2H, s), 7.264-7.357 (9H, m), 7.835 (1H, br s). δC (100 mHz, DMSO-D6) 46.419, 68.577, 128.976, 128.976, 130.860, 130.921, 131.471, 131.555, 136.239, 140.169, 142.977, 159.473. ESI+ 321 MNa+. HREIMS found 299.0854 C16H15N2O2S, requires 299.0854.

For large scale preps: N-Cbz 4-aminomethyl aniline (0.20 g, 0.8 mmol), DCM (8 mL) and triethyl amine (0.2 mL) in a round bottom flask that had been flame dried in the presence of molecular sieves and cooled under vacuum was stirred at 4° C. After 10 min di 2-pyridyl thionocarbonate (0.18 g, 0.8 mmol) was added. The reaction was stirred overnight at 4° C. after which time the DCM layer was washed twice with water and once with brine. Chromatography on silica gel yielded the titled compound (0.15 g, 63%) as a white solid with identical 1H NMR spectra to those above.

Synthesis of TU50

Following General Procedure 1, phenyl chlorothionoformate (0.7 mL, 4.2 mmol), N-Boc 4-aminomethyl aniline (1 g, 4.2 mmol), pyridine (20 mL), DMF (20 mL). Purification by chromatography on silica (2% EtOAc to 100% EtOAc) yielded the title compound as a white solid (120 mg, 10%). δH (400 mHz, DMSO-D6) 1.353 (9H, s), 4.088 (2H, d, J=6.0 Hz), 7.192-7.244 (3H, m), 7.336-7.392 (2H, m). δC (100 mHz, DMSO-D6) 31.364, 45.893, 81.113, 127.083, 127.427, 129.609, 132.913, 133.681, 137.610, 145.571, 158.885. ESI+ 287 MNa+. HREIMS found 265.1014 C13H17N2O2S, requires 265.1011.

For large scale preps: N-Boc 3-aminomethyl aniline (1.0 g, 4.5 mmol), DCM (15 mL) and triethyl amine (0.6 mL) in a round bottom flask that had been flame dried in the presence of molecular sieves and cooled under vacuum was stirred at 4° C. After 10 min di 2-pyridyl thionocarbonate (1.1 g, 4.5 mmol) was added. The reaction was stirred overnight at 4° C. after which time the DCM layer was washed twice with water and once with brine. Chromatography on silica gel yielded the titled compound (0.7 g, 59%) as a white solid with identical 1H NMR spectra to those above.

Synthesis of TU70

Following General Procedure 1, phenylchloro thionoformate (0.7 mL, 4.2 mmol), 2-naphthyl amine (0.6 g, 4.2 mmol), pyridine (20 mL), DMF (20 mL). Purification by chromatography on silica (2% EtOAc to 100% EtOAc) yielded the title compound as a white solid (38.5 mg, 5%). δH (400 mHz, CDCl$_3$) 7.295 (1H, dd, J=2.0, 8.8 Hz), 7.473-7.497 (2H, m), 7.667 (1H, d, J=2.0 Hz), 7.664-7.808 (3H, m).

Synthesis of TU71

N-Boc 3-(2'-amino)ethyl aniline (200 mg, 0.8 mmol), DCM (3 mL) and triethyl amine (0.15 mL) in a round bottom flask that had been flame dried in the presence of molecular sieves and cooled under vacuum was stirred at 4° C. After 10 min di 2-pyridyl thionocarbonate (200 mg, 0.8 mmol) was added. The reaction was stirred overnight at 4° C. after which time the DCM layer was washed twice with water and once with brine. Chromatography on silica gel yielded the titled compound (0.1 g, 59%) as a white solid. δH (400 mHz, CDCl$_3$) 1.405 (9H, s), 2.753 (2H, t, J=6.8 Hz), 3.327 (2H, q, J=6.8 Hz), 4.611 (1H, br s), 7.036-7.089 (3H, m), 7.228-7.266 (2H, m). δC (100 mHz, CDCl3) 28.65, 35.228, 41.301, 77.954, 133.806, 126.711, 129.006, 130.129, 133.727, 142.175, 155.936. m/z 279 (MH+). HREIMS found 279.1170 C14H19N2O2S, requires 279.1167.

EXAMPLE 3—General Materials and Methods (e.g., Pertaining to Example 4)

Materials

All materials were from Aldrich unless otherwise stated. 2-Dipyridyl thionocarbonate was from Acros (New Jersey, US). Phenyl chlorothionoformate, 4-chlorophenyl chlorothionoformate, 4-fluorophenyl chlorothionoformate, p-tolyl chlorothionoformate and [2-(4-aminophenyl)ethyl]carbamic acid tert butyl ester were from TCI America (Portland, Oreg.). 4-N-Cbz-aminomethylanilene was from astatech (Bristol, Pa.). AMC modified peptides were from BaChem (Torrance, Calif.). Mouse full length cathepsin C was from RnD systems (Minneapolis, Minn.). Recombinant human 20S proteasome was from Boston Biochem (Boston, Mass.). Alamar Blue® was from Invitrogen (Grand Island, N.J.). Bortezomib was from LC laboratories (Woburn, Mass.). Column chromatography was performed on silica gel (Siliaflash, Silicycle, Quebec, Canada) and TLC was performed on SiliaPlates and visualized by UV. NMR spectroscopy ($^1$H) was performed on a Bruker 400 MHz instrument in D$_3$CSOCD$_3$, CD$_3$OD, or CDCl$_3$. Deuterated solvents were purchased from Cambridge Isotope Laboratories (Cambridge, Mass.). DMEM, glutamax, penicillin/streptomycin were from Gibco (Grand Island, N.J.). Trypsin (0.25%) was from Hyclone (Logan, Utah). Bradford dye; Chill-out wax were from BioRad (Hercules, Calif.). Dithiothreitol reagent was from Gold Biotech (St Louis, Mo.). ECL II was from Pierce (Rockland, Ill.). Blue Biofilm was from Denville Scientific (Metuchen, N.J.). PVDF was from Millipore (Billerica, Mass.). LC/MS was performed on a Waters Acuity Ultra Performance LC with Waters MICROMASS detector. Transfection reagents were from Mirus. FACS analysis was carried out on a Becton Dickinson FACScalibur. Antibodies: anti-K48-linked ubiquitin, clone APU2; anti-K63-linked ubiquitin, clone APU3, were from Millipore (Billerica, Mass.); anti-SMAD4, H-552; anti-Mdm2, SC-13161 were from Santa Cruz (Santa Cruz, Tex.); anti-PARP, 9542; anti-Abl, 2862; B-tubulin, 2156 were from Cell Signaling Technologies (Beverley, Mass.). Anti-actin was clone AC-40, A3853 and anti-GAPDH was clone G9295. Anti-HA Clone 3F10 was from Roche (Indianapolis, Ind.). Annexin V apoptosis kit, anti USP7, UCHL5, USP9x (rabbit monoclonal) were from Abcam (Cambridge, Mass.) as were HRP labelled secondary antibodies.

HA-Ubiquitin-Vinylsulfone Activity Profiling.

Lysate labeling assay on untransfected cells (1.5 mg/mL lysate lysed using a Dounce homogenizer, 10 strokes, in 75 mM potassium phosphate pH 7.6, 150 mM NaCl, 0.75 mM BME) was run with the stated concentration of inhibitor (or 1% DMSO control) for 30 min. After this time HA-Ub-VS (1.5 µM) was added and incubated for 15 min. After this time reaction mixture (15 µL) was removed and quenched in 2× (final concentration) reducing Laemeli buffer. The reaction mixtures were heated to 37° C. for 10 min prior to analysis by western blot for HA. In select instances these data were replicated by blotting for the target enzyme (UCHL5, USP7 or USP9x) and observing the amount of HA-Ub-VS DUB complex formed. EC50s calculated by this method were in agreement with those found in the HA-blot.

UbG76V-GFP Proteasome Assay.

COS1 cells at approx. 75% confluence in a 48 well plate were transiently transfected with a plasmid encoding G76VUb-GFP using Mirus 2020 reagent. After this time media with either compound in DMSO or 1% DMSO was added to the cells and the cells were incubated for 8 h. After this time, cells were trypsinized, diluted with 1% FBS in PBS (FACS buffer) then centrifuged at 700 g. After this time cells on ice were treated with FACS buffer containing propidium iodide (0.05 mg/mL). The GFP (indicating proteasome activity) and red fluorescence (dye exclusion showing acute toxicity) were subsequently measured by FACS.

20S Proteasome Assay.

To recombinant human 20S proteasome (1.22 g/mL) in 50 mM potassium phosphate pH 7.6, 50 mM NaCl, 1 mM DTT was added the compound or DMSO. This mixture was incubated at 25° C. for 30 min after which time substrate (Suc-Leu-Leu-Val-Tyr-AMC, 100 µM or 17 µM) was added and release of AMC was measured as a function of time using a plate reader for 30 min. The steady state rates were calculated and normalized to the DMSO rate. The concentration of inhibitor required to inhibit the enzyme by 50% was calculated using prism.

Proliferation Assays

Proliferation assays for adherent cells were conducted by plating cells at 5%-10% confluence in 96 well plates together with compound or 0.1% DMSO. Cells were allowed to grow for 48 h and then Alamar Blue® was added and number of cells was measured by fluorescence on a microplate reader. For non-adherent cells, cells were grown in 24-well plates. Every 24 h, cells were agitated to ensure complete mixing. 4 h prior to measuring the number of viable cells, cells were agitated, then 100 µL aliquots were removed and added to a non-adherent 96 well plate. Alamar blue was then added and the plate read when required.

Progress Curve Analysis for Inhibition of USP9x by TUs

To Ub-AMC (300 nM) in 50 mM Hepes pH 7.7, 100 mM NaCl and the stated concentration of reducing agent at 37° C. was added inhibitor in 1% DMSO. Progress was measured every 2 min for 30-60 min. Curves were fit with dynafit to an irreversible inhibition mechanism.

$$E+S<==>ES$$

$$ES-->E+P$$

$$E+I-->EI$$

Fitting with a release parameter (EI==>E+I) showed no improvement to the fit.

Curve Fitting for Effect of Reducing Agent on Inhibition by TU49.

From the simple equilibrium $$RSH+TU49<==>\text{adduct } (kd)$$

$$TU49+E-->E.TU49\ (k_{on})$$

$$\text{Fraction adduct}=RSH/(kd+RSH)$$

$$k_{on}^{app}=k_{on}^0-k_{on}^0*\text{fraction adduct}$$

$$k_{on}^{app}=k_{on}^0-k_{on}^0*[RSH/(kd+RSH)]$$

EXAMPLE 4—Inhibition of DUBs

Aryl Isothiocyanates are Potent and Selective Inhibitors of USP9x

TU46, TU49, TU50 all showed significant inhibition of USP9x (FIG. 1, Table 2). Since 3-substitution appeared to be favored (TU50 was more potent than TU29), TU71, the meta-regioisomer of TU46, was also screened. Both compounds (TU46 and TU71) were equally effective, perhaps indicating that a longer linker can overcome the constraints of position selectivity on the aryl ring. At 85 µM TU46, TU49, TU50 and TU71 showed weak inhibition of other DUBs other than USP9x, most notably UCHL5. However below 25 µM these compounds showed little inhibition of other DUBs. TU49 was probably the most promiscuous inhibitor although this consistently showed the lowest $EC_{50}$. Repeated titrations of TU46, TU49, TU50 and TU71 showed that these compounds had 6-12 µM $EC_{50}$s for USP9x.

TABLE 2

| Data from FIG. 1 | | | |
|---|---|---|---|
| Cmpd | $EC_{50}$ (µM) | s.d. | n |
| TU46 | 12 | 2 | 4 |
| TU49 | 6 | 1 | 3 |
| TU50 | 9 | 5 | 4 |
| TU70 | 61 | 26 | 3 |
| TU71 | 9 | 4 | 2 |
| TU74 | 22 | 3 | 2 |
| TU76 | 131 | 60 | 3 |
| TU79 | 11 | 5 | 3 |
| TU81 | 20 | 14 | 2 |
| WP1130 | 3 | 1 | 3 |

A limited SAR study of the TUs was carried out using HA-Ub-VS profiling. On the whole these compounds were relatively selective for USP9x over most other DUBs providing an electron withdrawing group (m-F TU81; m-F,m-CN TU74, m-NO2 TU79) was present or a protected methyl amine. The least effective compounds were the 3-methyl substituted ITC, TU70, and the parent compound, TU76. These showed $EC_{50}$s>50 µM.

The commercially available cell permeable DUB inhibitor, WP1130, for comparison, had an $EC_{50}$ of 3 (±1) µM under similar conditions (FIG. 1, Panel C, Table 1). Other USPs were also inhibited under these conditions, consistent with the known promiscuity of WP11307. Although the ITCs were slightly less potent than WP1130, they were more selective for USP9x inhibition. The inhibition by our proprietary compounds was studied in more detail. This was because although fluoro, cyano and nitro derivatives were potent, electron withdrawing groups on the aryl ring are expected to destabilize the ITC to hydrolysis, and so the methylamino derivatives were expected to be the most hydrolytically stable.

Figure 2:
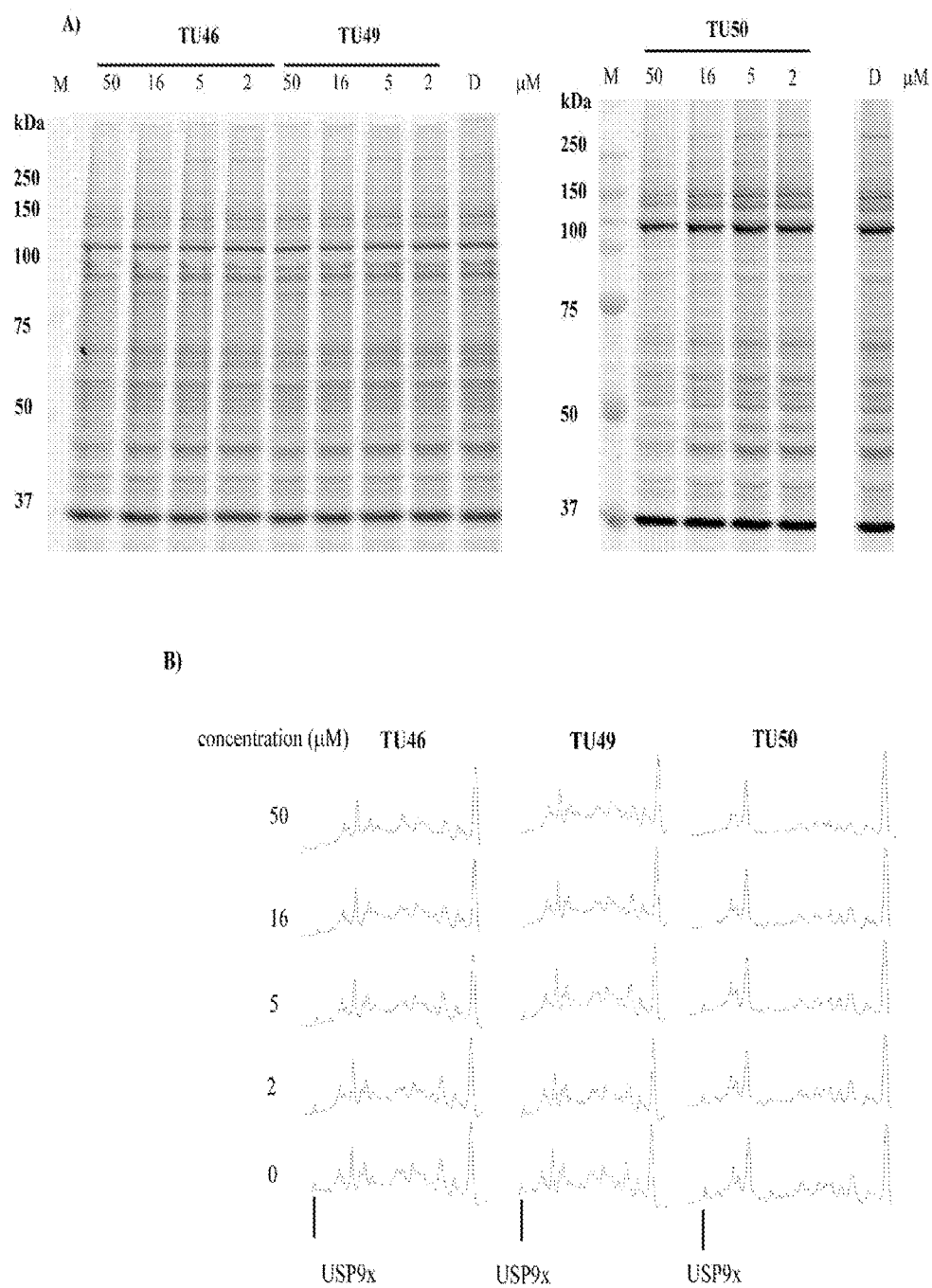
FIG. 2 has two panels (A and B) depicting data showing the effect of TU46, TU49, TU50 on Cy5-Ub-VME reactive proteins in BaF3 lysates. Panel A is an image of an immunoblot showing representative scans of lysates treated with compound for 15 min then Cy5-Ub-VME. Panel B is a plot of the bands in each lane using Image J processing and analysis software.

Using a Cy5-Ub-VME probe, many more bands were observed than under our typical assay conditions using HA-Ub-VS. A titration of a BaF3 lysate with TU50 followed by addition of Cy5-Ub-VME showed a similar $EC_{50}$ for USP9x inhibition to that measured with the HAubiquitin vinyl sulfone probe, validating that the two probes behave comparably in terms of their ability to assay USP9x under these conditions. Using Image J, the individual lanes from the lysates were plotted as a function of TU50 concentration. This analysis detects approximately 22 bands. The band corresponding to USP9x was clearly the most affected by TU50 (FIG. 2). TU46 and TU49 were also selective for USP9x. Only 5 proteins were significantly labelled by TU46 at 20 µM: 40S ribosomal protein S16; D-3-phosphoglycerate dehydrogenase; 40S ribosomal protein S4; 40S ribosomal protein S3; and 40S ribosomal protein S11. These proteins are all abundant and thus are prone to non-specific labeling. We Thus, TU46 is relatively selective for inhibition of DUBs.

TU46, TU49 and TU50 Inhibit Purified USP9x

Figure 3:
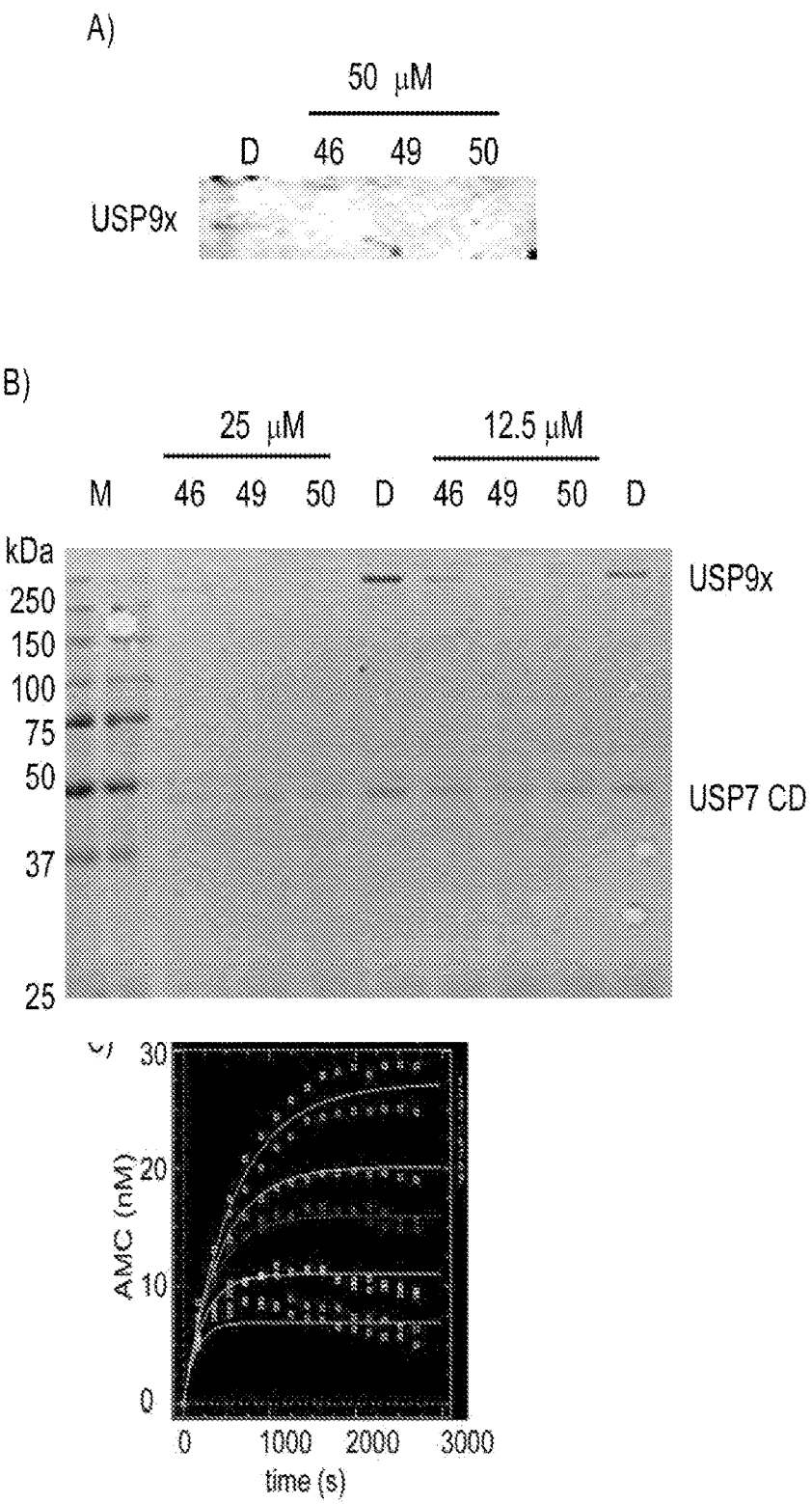
FIG. 3 has three panels (A, B, and C) depicting data showing that TU46, TU49, TU50 inhibit purified USP9x selectively. Panel A is an image showing that purified recombinant USP9x (7 nM) was treated with the stated compound at 50 μM for 19 min prior to addition of Cy5-Ub-VME for 5 min, then the mixture was resolved by S.D.S-PAGE and analyzed on a typhoon imager. Panel B is an image of an immunoblot showing purified recombinant USP9x (7 nM) and USP7CD (20 nM) were treated with the stated compound at the stated concentration for 19 min prior to addition of Cy5-Ub-VME for 5 min then the mixture was resolved by S.D.S-PAGE and analyzed on a Typhoon imager. Panel C shows a graph of AMC concentration (nM) as a function of time.

Preincubation of purified recombinant USP9x with TU46, TU49 or TU50 at 50 or 25 µM prior to activity profiling with Cy5-Ub-VME showed oblation of the fluorescent signal due to the formation of the USP9x-(Cy5-Ub-VME) complex (FIG. 3, Panel A). Repetition of this experiment in the presence of USP7 catalytic domain (USP7CD) together with USP9x, showed that little inhibition of USP7CD was observed at 12.5 µM by any of the 3 compounds studied, but USP9x was still strongly inhibited (FIG. 3, Panel B). These experiments were backed up by progress curve inhibition analysis for the inhibition of USP9x-catalyzed hydrolysis of Ub-AMC. On rates calculated from the progress curves indicated that all inhibitors bound the enzyme at a similar rate. Although this rate is relatively slow, it is comparable to $k_{on}$ calculated for WP1130 under similar conditions. In addition, the amount of free inhibitor is unknown and thus the true $k_{on}$ could be much higher.

Reducing Agents Sequester Free Inhibitor, Reducing Potency

Figure 4:
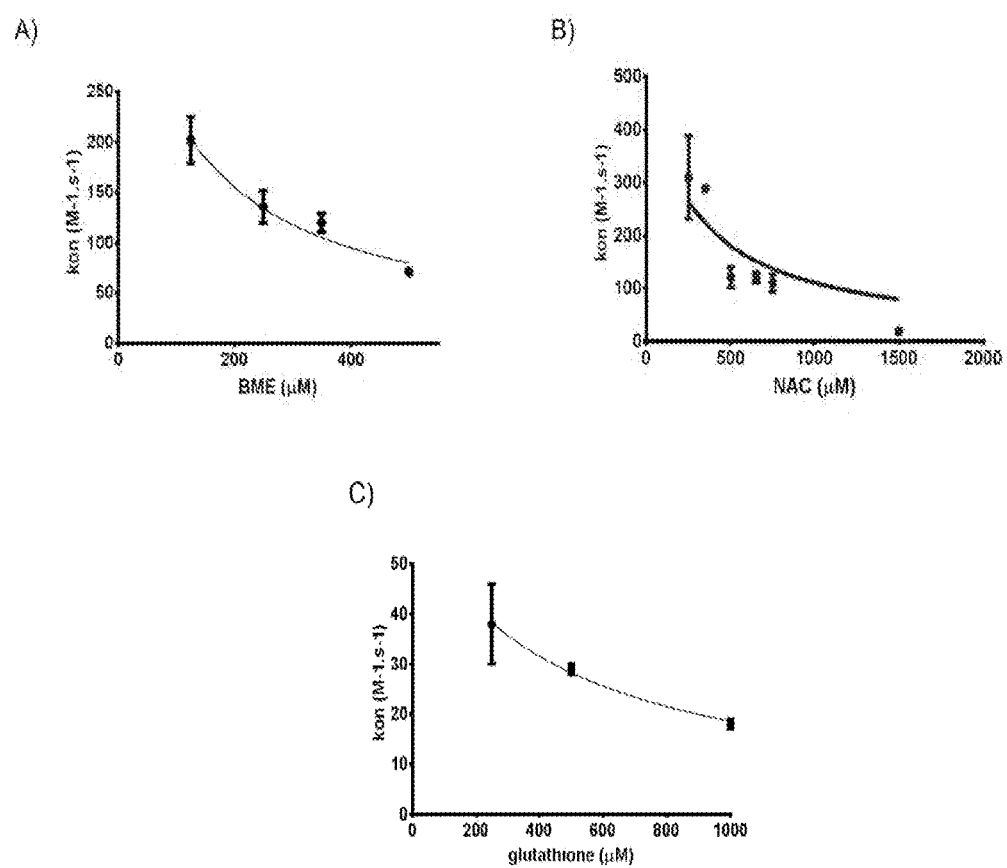
FIG. 4 has three panels (A, B, and C) depicting data showing that reducing agents mediate the potency of TU49. Purified recombinant USP9x (0.7 nM) was reacted with Ub-AMC (300 nM), TU49 (25 μM) and the stated concentration of BME (Panel A); N-acetyl cysteine (NAC) (Panel B); or glutathione (Panel C) and the amount of AMC released was measured. $K_{on}$ was calculated by curve fitting and plotted as a function of thiol present.

Working on the assumption that a significant percentage of the inhibitor was sequestered through the formation of reversible adducts with the reducing agent, the effect of reducing agent concentration on $k_{on}$ was assessed. Using rigorously degassed buffer maintained under $N_2$ until required for the assay, progress curves for the USP9x (0.7 nM)-catalyzed hydrolysis of ubiquitin-AMC with TU49 (25 µM) in the presence of 500, 350, 250, 125 µM BME were obtained (FIG. 4, Panel A). A clear inverse relationship was observed between reducing agent and $k_{on}$. Using a simple equation, derived in materials and methods, the $k_{on}^0$ (the $k_{on}$ when there is no reducing agent) was extrapolated to be 430±100 M-1 s-1 in BME. The $k_d$ was calculated to be 120±40 µM. When N-acetyl cysteine was used as a reducing agent, $k_{on}^0$ and $k_d$ could not be mutually parsed out, but forcing $k_{on}^0$ to be 430 M-1 s-1 gave a reasonable fit, with a $k_d$=280±50 µM. In the presence of glutathione, inhibition was overall slower than with BME or NAC. However, the dependence of $k_{on}$ on glutathione was less significant and inhibition was still observed at 1000 µM (FIG. 4, Panel B). A similar extrapolation to that shown above gave a $k_{on}^0$ 60±4 µM, with a $k_d$ of 450±70 µM for glutathione. The differences between NAC/BME and glutathione could be due to the free amino function in glutathione enabling the formation of chelated structures, or a slow, irreversible migration of the ITC from S to N within glutathione. In any case, these data show that inhibition by TU-type compounds is complex and simple in vitro models may not be able to predict inhibition behavior in cells.

Aryl Isothiocyanates Selectively Reduce Proliferation of Cancer Cells, Particularly Those Overexpressing Bcr-Abl The more potent N-protected methylamino TUs (TU46, TU49, TU50 and TU71) were assayed for growth inhibition of BaF3/p210 cells. This cell line consists of engineered murine leukemia cells that ectopically express Bcr-Abl. Parent BaF3 cells require exogenous interleukin 3 (IL3) because IL3 stimulates expression of MCL1, which is required for survival. However, BaF3/p210 cells require no exogenous interleukins but need Bcr-Abl for survival. TU46, TU49, TU50 all showed good growth inhibition against BaF3/p210 cells. Importantly the efficacy these compounds showed in the cell was similar to the $EC_{50}$ we calculated using the VS assay. TU71 did not show a significant growth inhibition until very high concentrations and was not investigated further.

Figure 5:
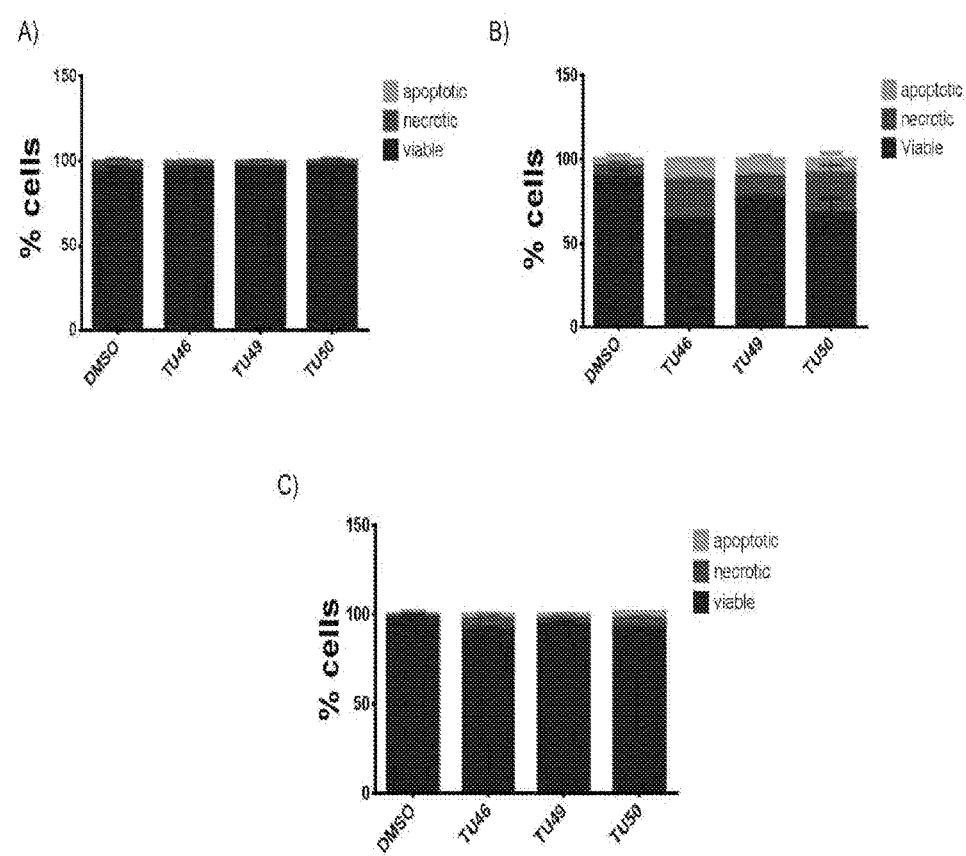
FIG. 5 has three panels (A, B, and C) depicting data showing that TU46, TU49 and TU50 initiate apoptosis in K562 but not HeLa cells. Cells were treated with DMSO, TU46, TU49 or TU50 for 24 h then analyzed using Annexin V-FITC and PI. (each point is shown as mean+/−s.d. of 2 replicates). Panel A is a bar graph showing the data for HeLa cells (30 μM); Panel B is a bar graph showing the data for K562 (30 μM); Panel C is a bar graph showing the data for K562 (15 μM).

Since TU46 and TU50 were most effective against BaF3/p210 these compounds were screened against an assortment of cell lines (FIG. 5, Panels A and B). Both TU46 and TU50 showed at least a five-fold selectivity for BaF3/p210 over other cancer lines. In the case of NIH3T3 cells, over a ten-fold selectivity was observed. To test the duration of efficacy of TU46 and TU50, BaF3/p210 cells were plated with compound and after 24 h media was diluted with fresh media containing TU46 or TU50 at the original concentration. After 24 h further growth, the number of viable cells was determined using Alamar Blue. $EC_{50}$ for TU46 was 11 µM and for TU50 was 16 µM (these values are not included in the values in FIG. 4, Panel C). Since the $EC_{50}$s did not decrease when fresh compound was added after 24 h, it is likely that the concentration of the compounds does not change significantly over the course of the assay. BaF3/p210 cells grow relatively quickly and comparisons of toxicity for these lines relative to slower growing adherent lines can be misleading. See for example, Chauhan et al., Cancer Cell 22, 345-358 (2012). Since good evidence was obtained that the TU compounds are stable under the assay conditions, the 48 h proliferation inhibition for BaF3/p210 cells was compared against a range of other cell lines grown for 72 h in the presence of TU46 or TU50. Even under these conditions, an $EC_{50}$ of >110 µM (TU46) and 80±10 µM (TU50) was observed for 3T3 and 70±20 µM (TU46) 85±10 µM (TU50) was observed for B16-F10. TU49 showed low growth inhibition against 3T3 at the 72 h time point >110 µM. Interestingly, TU49 showed around a 30 µM $EC_{50}$ for growth inhibition of B16-F10 at this time point. On the other hand, WP1130 showed similar $EC_{50}$s for HeLa, 3T3, B16-F10 and MCF7 (3 µM). This implies that WP1130 has little selectivity for any cell line, consistent with the known non-specific reactivity of this compound. See Altun et al., Chemistry & Biology 18, 1401-1412 (2011). All in all our ITCs compare favorably with WP1130 in terms of their toxicity spectrum, potency and efficacy.

Figure 6:
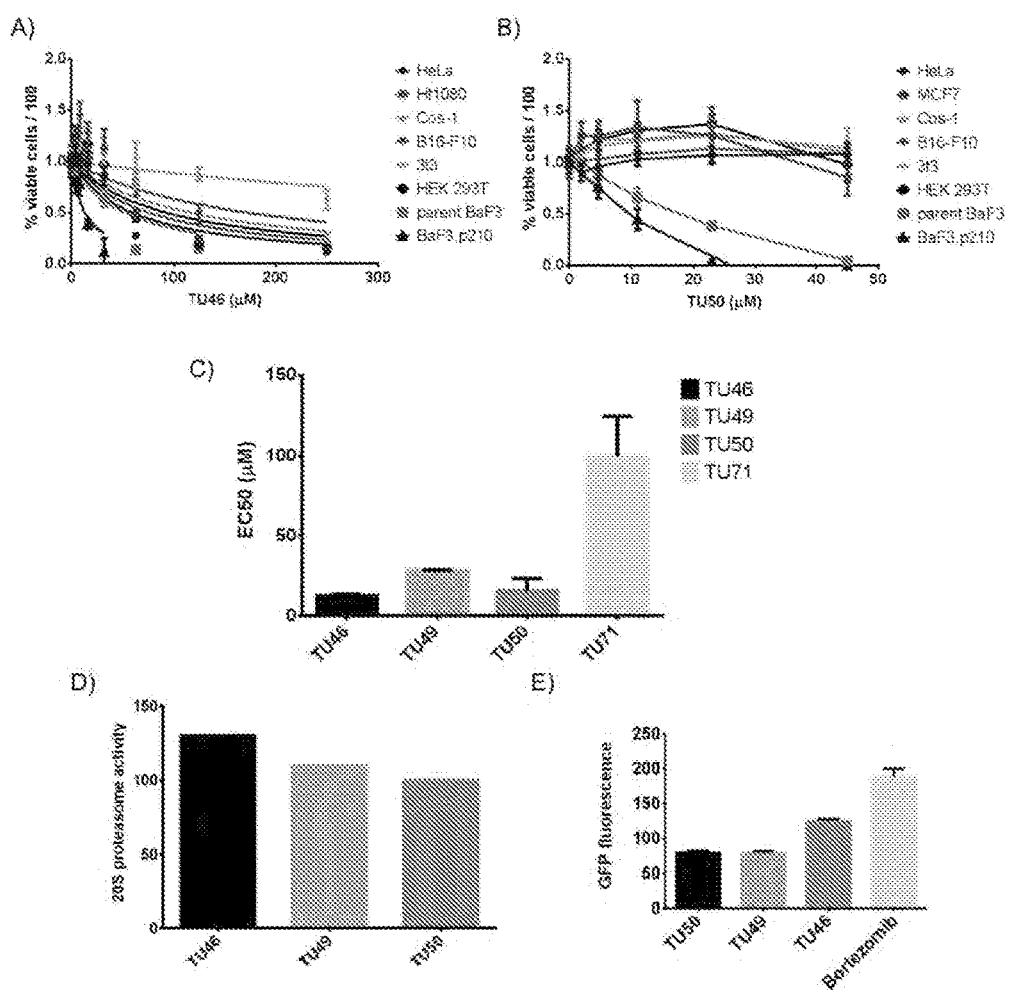
FIG. 6 has five panels (A, B, C, D, and E) depicting data showing that TU46 and TU50 are selective inhibitors of BaF3/p210 cell growth. Varying concentrations of TU46 (Panel A) or TU50 (Panel B) were added to the stated cell line and after 48 h the number of viable cells was calculated using Alamar Blue. Panel C is a bar graph showing $EC_{50}$s for growth inhibition of BaF3/p210 cells by TU compounds (TU46, TU50 n=3; TU49 n=2; TU71 n=1; each n represents a titration of at least five concentrations with each concentration replicated at least five times). Panel D is a bar graph showing that TU46, TU49, TU50 (50 μM) do not inhibit the purified 20S proteasome-catalyzed hydrolysis of Suc-Leu-Leu-Val-Tyr-AMC. Panel E is a bar graph showing COS1 cells were transfected with G76VUb-GFP, then treated with TU46, TU49 or TU50 (85 μM) for 8 h after which time GFP was measured by FACS (each point is shown as mean±s.d. of 3 replicates).

Since K562 cells are dependent upon Bcr-Abl for survival, it was predicted that these cells would also be susceptible to TU compounds. However, K562 cells gave a very weak signal in the Alamar Blue® assay. In lieu of the Alamar Blue assay, an apoptosis assay was used to show susceptibility. This assay uses fluorescein-modified Annexin V to detect phosphatidyl serine (PS) on the cell surface. See Vermes et al., J. Immon. Meth. 184, 39-51 (1995). PS is typically expressed on the inner leaflet of the cell membrane. However in the early stages of apoptosis, PS translocates to the outer leaflet and can be bound by Annexin V. Thus, during apoptosis cells will become greener in the presence of Annexin V-Fluorescine. Consistent with the data above, no apoptosis was detected in HeLa treated with TU46, TU49 or TU50 (15 or 30 μM) for 24 h (FIG. 6, Panel A). However, treatment of K562 cells with TU46, TU49 or TU50 under the same conditions caused a large increase in both apoptosis and necrosis (FIG. 6, Panels B and C).

Aryl Isothiocyanates Do Not Inhibit the Proteasome

TU46, TU49, TU50 did not inhibit the proteasome either in a pure 20S proteasome assay or in a G76VUb-GFP assay in COS1 (FIG. 6, Panels D and E). In the G76VUb-GFP assay, TU49 and TU50, decreased the GFP signal, consistent with DUB inhibition. At 50 μM TU46 there was a slight increase in GFP signal which may indicate that TU46 inhibits a different spectrum of target proteins than TU49 or TU50. Bortezomib, the positive control showed a two-fold increase in GFP signal as has been previously reported. See Um et al., J Neurosci. 30, 11805-11814 (2010).

Aryl Isothiocyanates Cause Knockdown of Bcr-Abl in BaF3/p210

Figure 7:
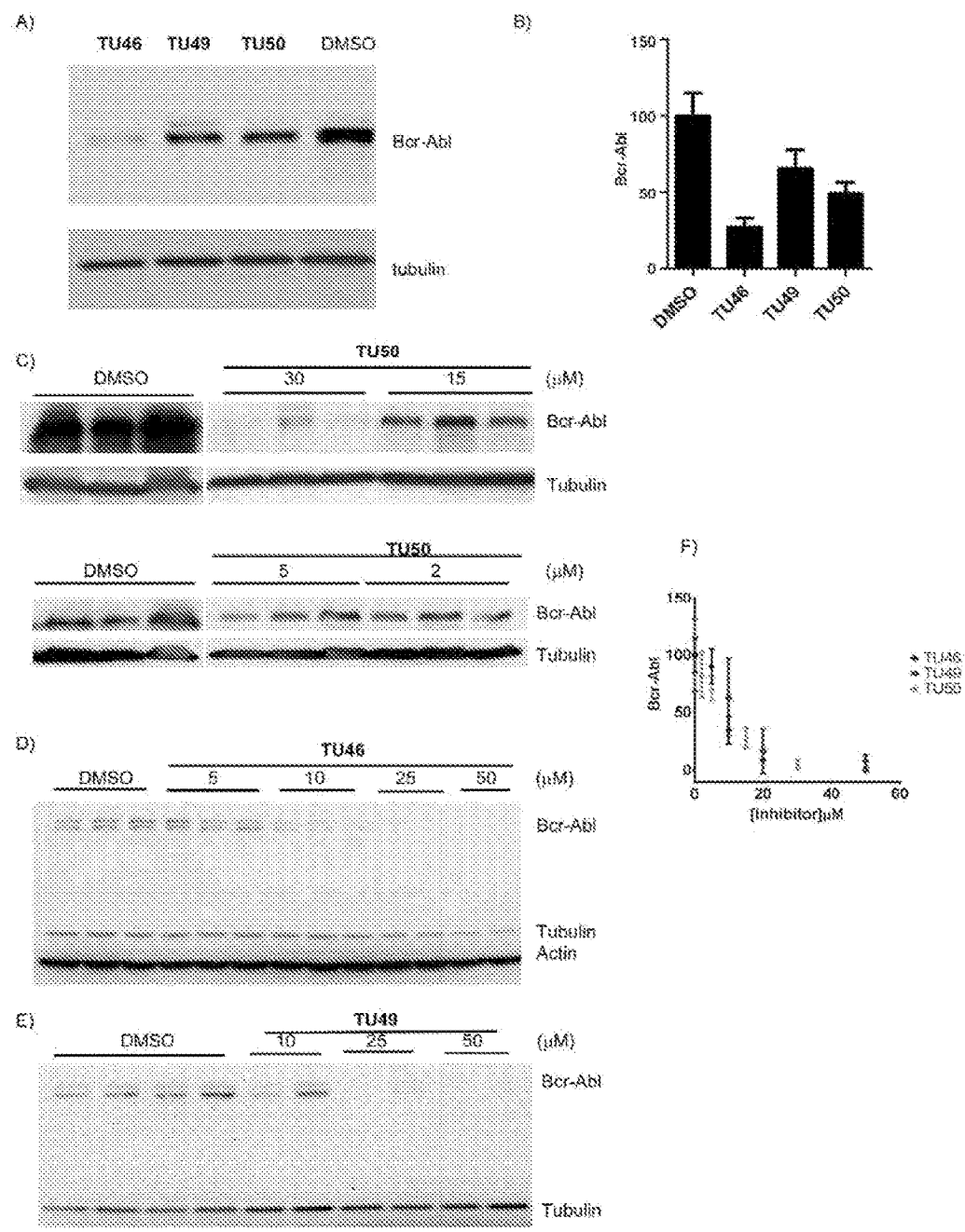
FIG. 7 has six panels (A, B, C, D, E, and F) depicting data showing that TU46, TU49 and TU50 cause degradation of Bcr-Abl in BaF3/p210 cells. Panel A is an image of an immunoblot showing BaF3/p210 cells were treated with 15 μM TU46, TU49 or TU50 for 4 h. After this time cells were lysed and sonicated in S.D.S. Whole cell lysates were analyzed for Bcr-Abl and tubulin in triplicate. Panel B is a bar graph showing the quantitation of blots in Panel A. Panel C is an image of an immunoblot showing BaF3 cells were treated with various concentrations of TU50 in triplicate for 4 h, and then whole cell lysates were analyzed for Bcr-Abl and tubulin. Panel D is an image of an immunoblot similar to the experiment in Panel C but using TU46. Panel E is an image of an immunoblot similar to the experiment in Panel D but using TU49. Panel F is a plot showing the quantification of blots in Panel C, Panel D, and Panel E.

Proliferation inhibition/apoptosis assays and lysate activity profiling were all consistent with USP9x inhibition. Next, whether cell death in BaF3/p210 cells occurred through degradation of Bcr-Abl was validated. BaF3/p210 cells were treated with compound (15 μM, within two fold of the growth proliferation $EC_{50}$ for these compounds) for 4 h then harvested and analyzed for Bcr-Abl expression. Consistent with their similar growth inhibition properties for BaF3/p210 cells, TU46, TU49, and TU50 caused 50-75% loss of Bcr-Abl in this time period (FIG. 7, Panels, A and B). Encouragingly, the $EC_{50}$ for Bcr-Abl degradation was 8±2 μM for TU50, which is within 2 fold of the proliferation inhibition $EC_{50}$ obtained above (FIG. 7, Panel C). TU46 had an $EC_{50}$ for Bcr-Abl knockdown of 9±3 μM (15±7 μM when unsonicated) and TU49 had an $EC_{50}$ of 9±5 μM (FIG. 7, Panels D, E, and F).

Figure 8:
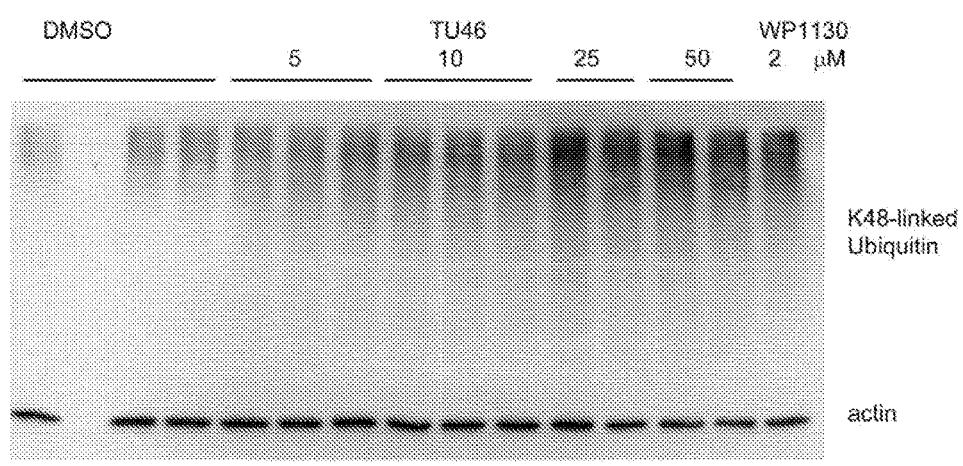
FIG. 8 has two panels (A and B) depicting data showing that TU46 increases K48-linked ubiquitin at similar concentrations to which Bcr-Abl is knocked down. Panel A is an image of an immunoblot showing BaF3/p210 cells were treated with various concentrations of TU46 for 4 h, and then whole cell lysates were blotted for K48-linked ubiquitin and tubulin. Panel B is an immunoblot showing same lysates as in Panel A were blotted for Bcr-Abl.
Figure 8:
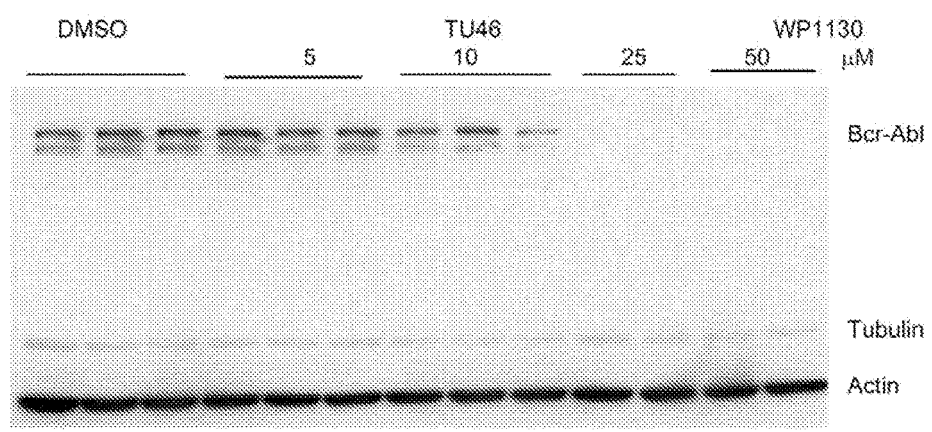

The K48-linked ubiquitin levels were also probed in these lysates. Although in vitro assays showed that many TU compounds were selective inhibitors of USP9x, K48 levels were increased by this compound in a dose dependent manner (FIG. 8, Panel A). The increase in K48-linked ubiquitin coincided with the loss of Bcr-Abl (FIG. 8, Panel B). Since USP9x is known to deubiquitinate K48-linked polyubiquitin chains, it is possible that this increase in K48-linked ubiquitin is due to USP9x inhibition. See Park et al., PNAS 110, 9433-9438 (2013). However, it is also possible that the longer time of the cell based assay (4 h) relative to the in vitro assay allowed inhibition of other targets to occur.

Aryl Isothiocyanates Inhibit Numerous DUBs in Cells

Figure 9:
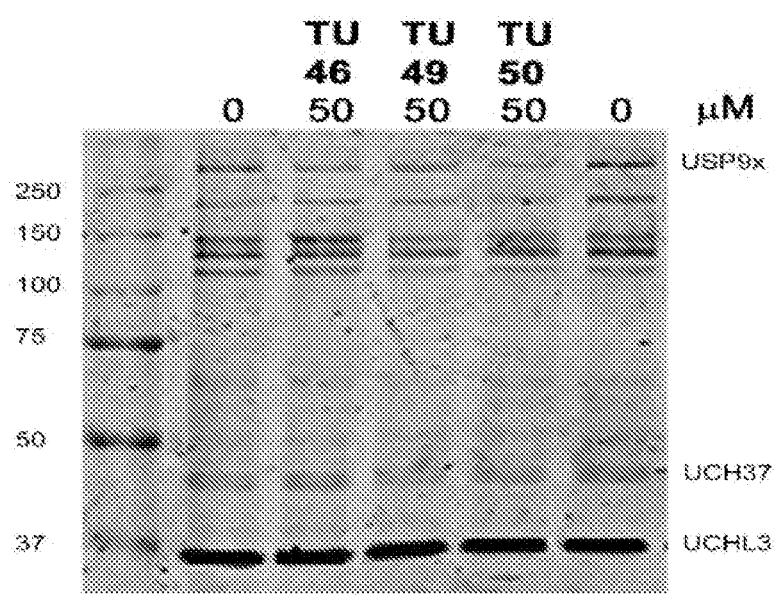
FIG. 9 has two panels (A and B) depicting data showing that TUs inhibit DUBs in cells. BaF3/p210 cells were incubated with the stated concentration of compound for 4 h. After this time cells were lysed using beads, lysates were normalized, then exposed to Cy5-Ub-VME for 5 min. After quenching, lysates were resolved by SDS-PAGE, analyzed on typhoon, then stained by Coomassie. Panel A is an image of the SDS-PAGE gel visualized via Typhoon imager. Panel B is an image of the SDS PAGE gel stained with Coomassie.
Figure 9:
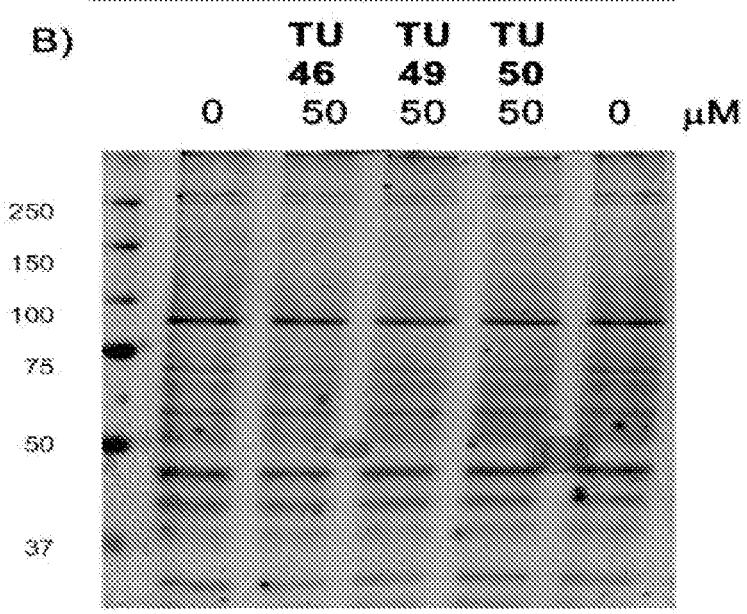

To further investigate the reason behind the increase in HMW ubiquitin, activity profiling of BaF3/p210 cells treated with 50 μM TU46, TU49 or TU50 for 4 h was carried out (FIG. 9). Treatment of the lysate with Cy5-Ub-VME showed a decrease in a number of bands in addition to the band corresponding to USP9x. UCHL3 was relatively unaffected by all inhibitors studied and served as a loading control (Coomassie staining of the gel also is consistent with equal loading). The increased promiscuity of the inhibitors when the experiment is carried out in cells likely stems from the increased assay time (4 h vs 20 min) coupled with the slow on rates of the inhibitors and their targets. Thus selectivity observed in lysate assays is probably a kinetic phenomenon and does not necessarily reflect the true affinity Aryl Isothiocyanates Cause Knockdown of Bcr-Abl in K562

Figure 10:
FIG. 10 has three panels (A, B, and C) depicting data showing that TU46, TU49 and TU50 cause degradation of Bcr-Abl in K562 cells. Panel A is an image of an immunoblot showing 30 μM TU46, TU49 or TU50 was added to K562 for 4 h. After this time cells were lysed and sonicated in SDS. Whole cell lysates were analyzed for Bcr-Abl and tubulin in triplicate. Panel B is a bar graph showing the quantitation of the blots in Panel A. Panel C is a plot showing differing concentrations of TU50 were added to K562 cells and after 4 h the amount of Bcr-Abl was measured in whole cell lysates.
Figure 10:
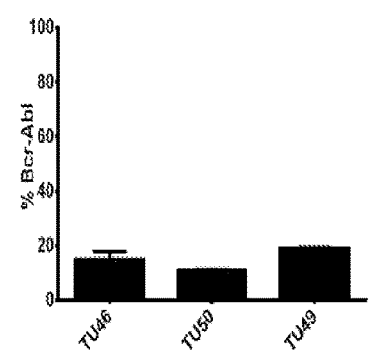
Figure 10:
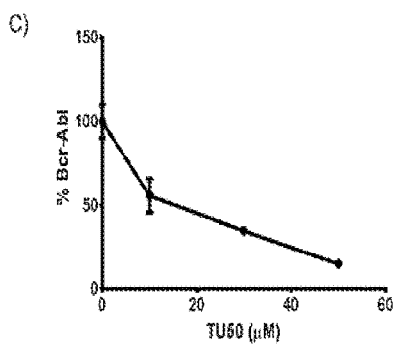

Since the compounds were also toxic to K562 cells, the effect of TU46, TU49 and TU50 on Bcr-Abl levels in K562 cells was also assessed. Treatment of K562 cells with 30 μM TU46, TU49, TU50 caused a four-fold decrease in Bcr-Abl in 4 h (FIG. 10, Panels A and B). Titration of K562 with TU50 showed that the $EC_{50}$ for Bcr-Abl degradation was 12 μM, consistent with the $EC_{50}$ for USP9x inhibition and the $EC_{50}$ for Bcr-Abl degradation observed in BaF3/p210 cells (FIG. 10, Panel C).

Aryl Isothiocyantes Cause Knockdown of MCL1

Figure 11:
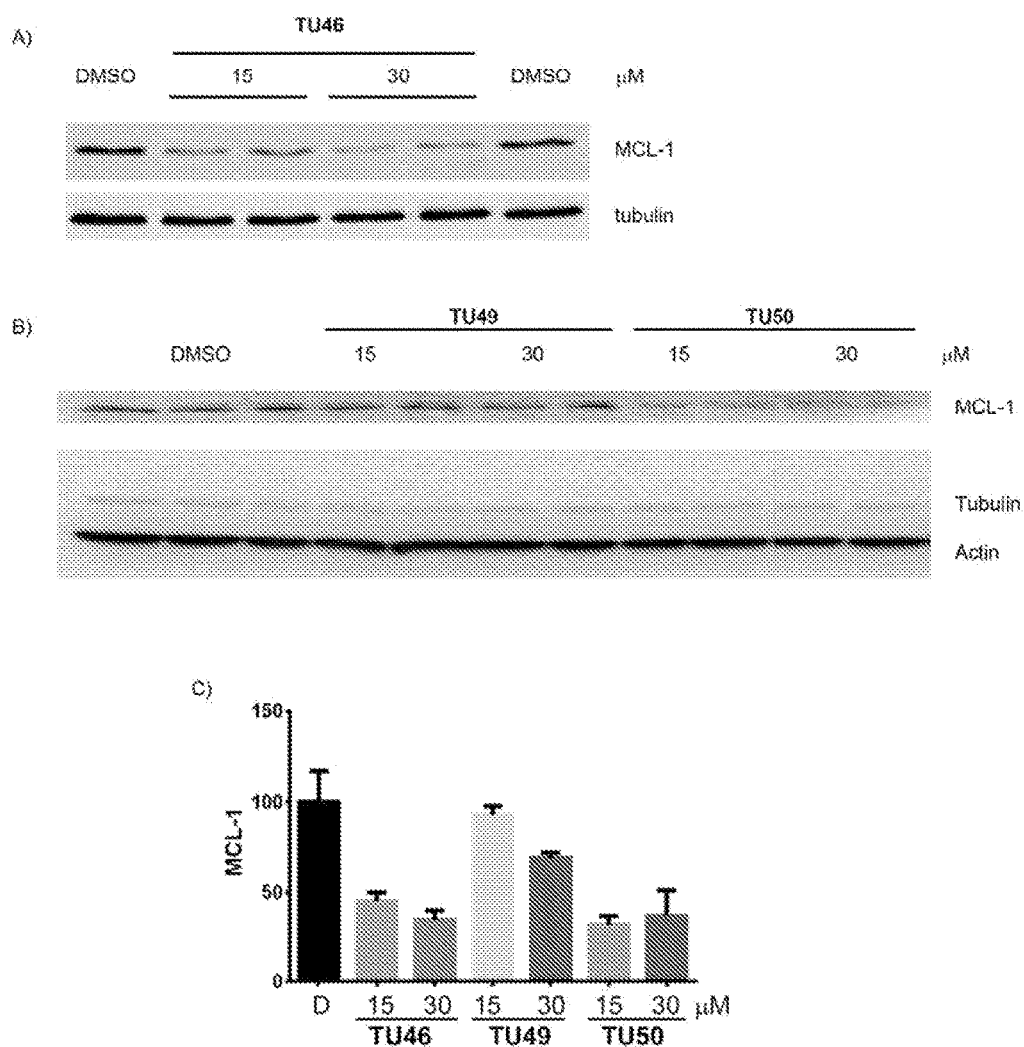
FIG. 11 has three panels (A, B, and C) depicting data showing TU46, TU49 and TU50 cause degradation of MCL-1 in BAF3 cells in 4 h. Panel A is an image of a immunoblot showing knockdown of MCL-1 by TU46. Panel B is an image of an immunoblot showing knockdown of MCL1 by TU49 and TU50. Panel C is a bar graph showing the quantitation of the blots in Panel A and Panel B.

Growth inhibition assays above, showed that BaF3 parent were also susceptible to TU46 and TU50 at higher concentrations than BaF3/p210. MCL1 is required to sustain growth of many transformed cells and is also regulated by USP9x. We thus treated BaF3 parent cells with TU46, TU49 or TU50 (15 and 30 μM) and blotted for MCL1. TU46 and TU50 were both very effective at knocking down MCL1, whereas, TU49 was not as efficient (FIG. 11, Panels A, B, and C). These findings help to explain why these compounds are toxic to Bcr-Abl independent cancer lines, especially BaF3.

EXAMPLE 5—Thioimidocarbonic Acid Diesters as Cathepsin C Inhibitors

Figure 12:
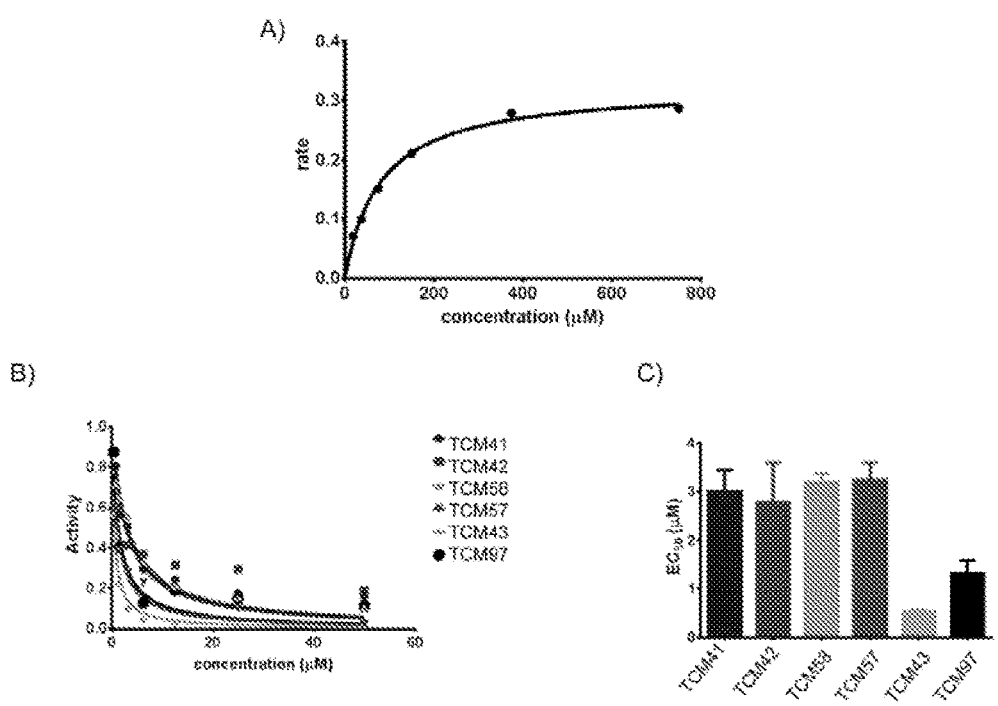
FIG. 12 has three panels (A, B, and C) depicting data showing that certain thioimidocarbonic acid diesters of the invention inhibit cathepsin C. Panel A is a plot showing the $K_M$ calculation for cathepsin C and substrate, Gly-Phe-AMC. Panel B is a plot showing Cathepsin C was incubated with the stated compound for 30 min prior to addition of substrate and residual activity was measured. Panel C is a plot showing the $EC_{50}$ values calculated from Panel B.
Figure 13:
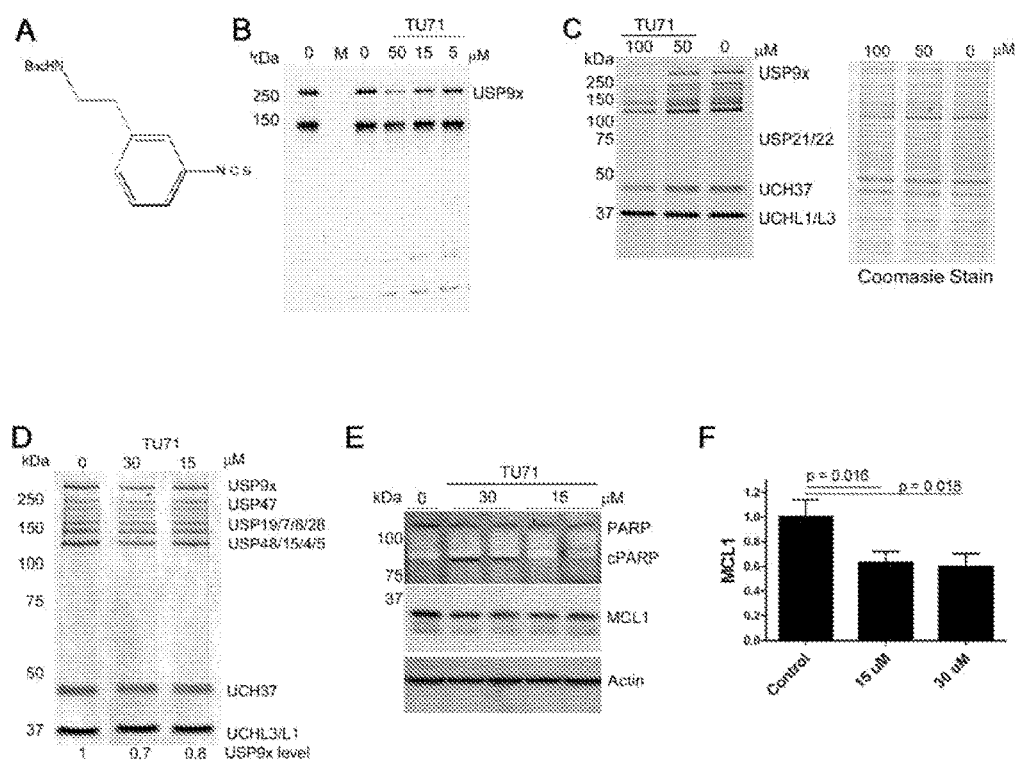
FIG. 13 has six panels (A, B, C, D, E, and F) showing that isothiocyanate TU71 inhibits DUBs, decreases the level of oncogenic pre-survival protein, MCL-1, and initiates apoptosis in BaF3/p210 cells. Panel A is the chemical structure of TU71. Panel B is an image of an immunoblot showing a K562 cell was treated with TU71 for 15 min at which time HAUb-VS was added. After an additional 15 min, aliquots were quenched in reducing loading buffer and analyzed by SDS-PAGE and HA blot. The $EC_{50}$ for USP9x inhibition was determined to be 20±1 μM. BaF3/p21 0 cells were treated with TU71 for 2.5 h (Panel C) or 4 h (Panel D). Cells were harvested, lysed and incubated (0.7 mg/mL protein) with 250 nM Cy5-UbVME for 5 min at 37° C. Panel C also shows (on the left) an image of an in-gel fluorescent scan obtained on GE Typhoon scanner and (on the right) a Coomassie-stained gel demonstrating equal loading. Panel E is an image of an immunoblot showing BaF3/p210 cells were incubated with TU71 for 4 h. The cells were harvested, lysed, analyzed by SDS-PAGE and immunoblotted as indicated. "cPARP" indicates the caspase cleavage of product of PARP and is indicative of apoptosis. Panel F is a bar graph showing data representative of mean±range of two independent experiments, one performed in duplicate of the blot depicted in Panel E.
Figure 14:
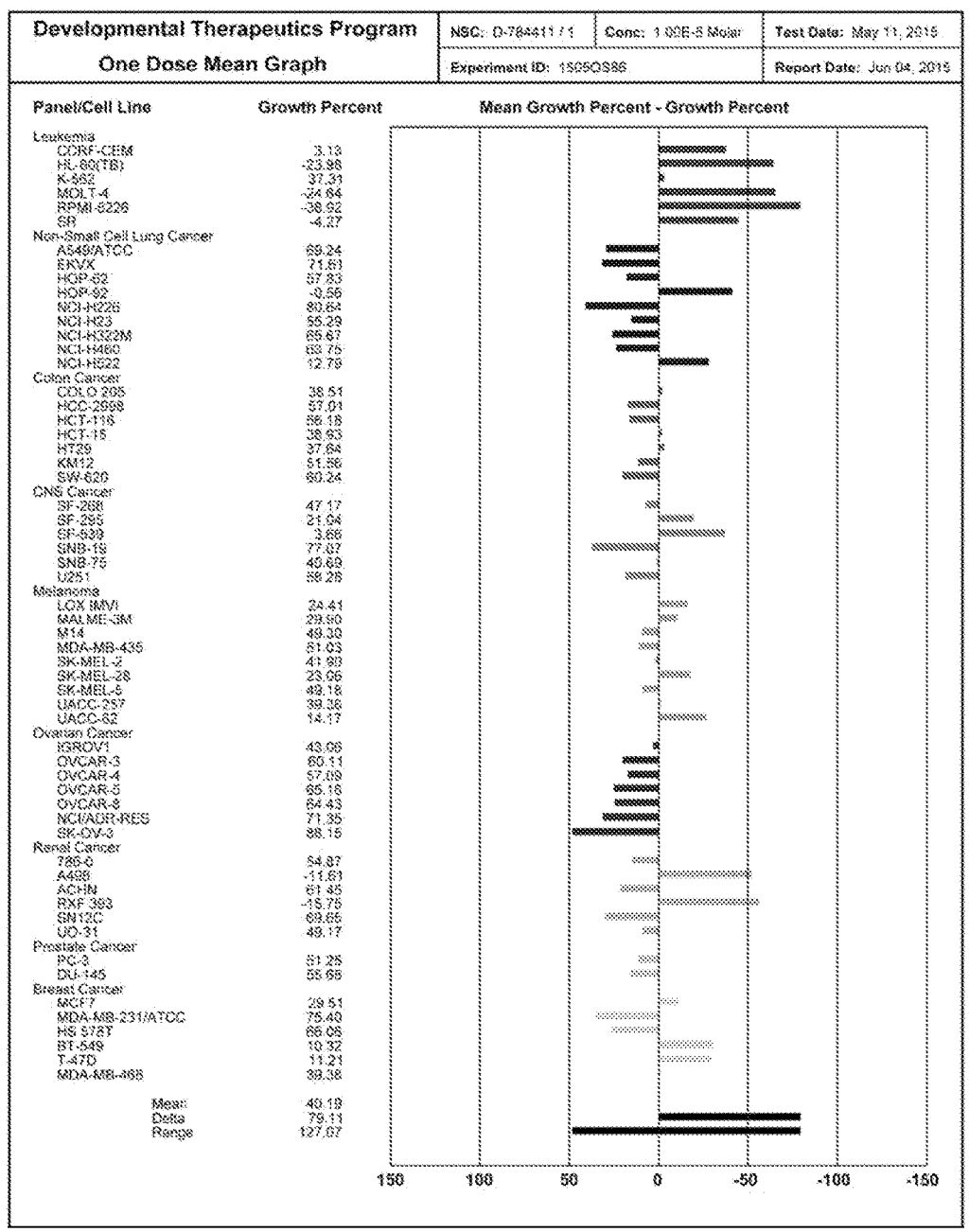
FIG. 14 shows the NCI 60 cell screened data for TU50. TU50 exhibits selective lethality against leukemic cell lines when tested in the NCI-60 human tumor cell line screen.

Cathepsin C is an enzyme important in inflammation. Screening certain compounds of the invention revealed various interesting sets of cathepsin C inhibitors. The assay was undertaken by incubating the enzyme in the presence of compound for 30 min, then adding substrate (150 μM; kM=75 μM) and measuring residual activity. The most potent cathepsin C inhibitors were thioimidocarbonic acid diesters, such as TCM40. TCM41, TCM42, TCM58, TCM43, and TCM97 (FIG. 12). These compounds all had an $EC_{50}$ for cathepsin C inhibition in the low micromolar range. A positive charge on the inhibitor appeared to be the most favorable for inhibition, because TCM43 bearing a p-NME2 substituent on the aniline moiety was the most potent inhibitor. Furthermore, substitution in the 3-position of the aniline function appeared to be more favored than 4-substitution (TCM97 vs TCM41). However substitution on the phenyl ester function was much less important for inhibition, with chloro, fluoro and proton all giving similar inhibition potencies.

Thioimidocarbonic acid diesters are interesting for a number of reasons. Firstly, these compounds are not well documented and their biological properties are thus not well understood. Furthermore, because of the extensive characterization of various cysteine proteases, thioimidocarbonic acid diesters may not be good inhibitors of DUBs or papain/ficin. They also did not inhibit the pure 20S proteasome. Thus these compounds are of interest as "specific" cathepsin C inhibitors.

INCORPORATION BY REFERENCE

All of the U.S. patents and U.S. patent application publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A compound selected from the group consisting of:

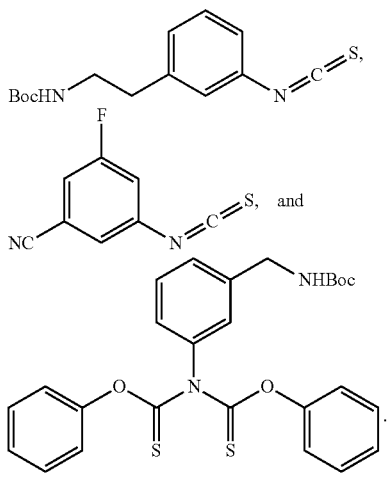

2. A method of treating a cancer, comprising the step of: administering to a subject in need thereof a therapeutically effective amount of a compound selected from the group consisting of:

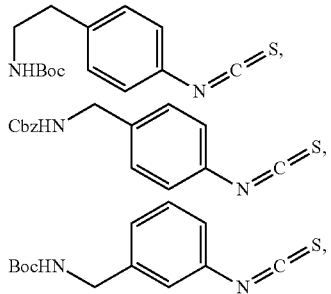

-continued

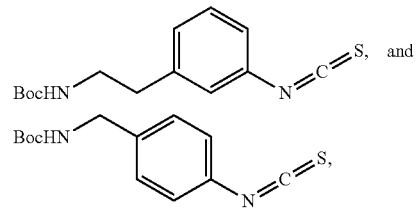

wherein the cancer is leukemia, myeloma, lung cancer, colon cancer, central nervous system (CNS) cancer, melanoma, ovarian cancer, renal cancer, prostate cancer, or breast cancer.

3. The method of claim 2, wherein the cancer is leukemia or myeloma.

4. The method of claim 2, wherein the compound is

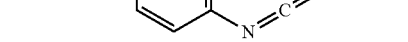

5. The compound of claim 1, wherein the compound is selected from the group consisting of:

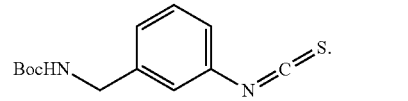

6. The method of claim 2, wherein the cancer is leukemia.

7. The method of claim 2, wherein the cancer is myeloma.

* * * * *